US012577323B2

(12) United States Patent
Galipeau et al.

(10) Patent No.: US 12,577,323 B2
(45) Date of Patent: Mar. 17, 2026

(54) COMPOSITIONS AND CONJUGATES COMPRISING AN INTERLEUKIN AND POLYPEPTIDES THAT SPECIFICALLY BIND TGF-BETA

(71) Applicants: Emory University, Atlanta, GA (US); Children's Healthcare of Atlanta, Inc., Atlanta, GA (US)

(72) Inventors: Jacques Galipeau, Atlanta, GA (US); Spencer Ng, Atlanta, GA (US)

(73) Assignees: Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 0 days.

(21) Appl. No.: 15/735,158

(22) PCT Filed: Jun. 8, 2016

(86) PCT No.: PCT/US2016/036358
§ 371 (c)(1),
(2) Date: Dec. 8, 2017

(87) PCT Pub. No.: WO2016/200881
PCT Pub. Date: Dec. 15, 2016

(65) Prior Publication Data
US 2018/0155439 A1     Jun. 7, 2018

Related U.S. Application Data

(60) Provisional application No. 62/173,592, filed on Jun. 10, 2015.

(51) Int. Cl.
| | |
|---|---|
| *C07K 14/54* | (2006.01) |
| *A61K 38/17* | (2006.01) |
| *A61K 38/20* | (2006.01) |
| *A61P 35/00* | (2006.01) |
| *C07K 14/495* | (2006.01) |
| *C07K 14/71* | (2006.01) |
| *C07K 14/715* | (2006.01) |
| *C07K 16/30* | (2006.01) |
| *C07K 16/32* | (2006.01) |
| *C12N 15/63* | (2006.01) |

(52) U.S. Cl.
CPC ............ *C07K 16/32* (2013.01); *A61K 38/179* (2013.01); *A61K 38/1793* (2013.01); *A61K 38/2086* (2013.01); *A61P 35/00* (2018.01); *C07K 14/495* (2013.01); *C07K 14/54* (2013.01); *C07K 14/5443* (2013.01); *C07K 14/71* (2013.01); *C07K 14/7155* (2013.01); *C07K 16/30* (2013.01); *C12N 15/63* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 7,947,265 | B2 | 5/2011 | Galipeau |
| 8,163,879 | B2 | 4/2012 | Wong |
| 8,771,664 | B2 | 7/2014 | Lopez |
| 2005/0053579 | A1 | 3/2005 | Galipeau |
| 2006/0269526 | A1 | 11/2006 | Galipeau |
| 2010/0021421 | A1 | 1/2010 | Galipeau |
| 2011/0177070 | A1 | 7/2011 | Lofquist |
| 2017/0073387 | A1 | 3/2017 | Galipeau |

FOREIGN PATENT DOCUMENTS

| | | |
|---|---|---|
| EP | 2511294 A2 | 10/2012 |
| WO | 2005100395 | 10/2005 |
| WO | 2009152610 | 12/2009 |
| WO | 2012040323 | 3/2012 |
| WO | 2012175222 | 12/2012 |
| WO | 2015018528 | 2/2015 |

OTHER PUBLICATIONS

Wells, 1990, Biochemistry 29:8509-8517.*
Bork, 2000, Genome Research 10:398-400.*
Skolnick et al., 2000, Trends in Biotech. 18(1):34-39.*
Doerks et al., 1998, Trends in Genetics 14:248-250.*
Tokuriki and Tawflik, Current Opinion in Structural Biology 2009, 19: 596-604.*
Benahmed et al. Inhibition of TGF-beta Signaling by IL-15: A New Role for IL-15 in the Loss of Immune Homeostasis in Celiac Disease, Gastroenterology 2007, 132:994-1008.
Bessard et al. High antitumor activity of RLI, an interleukin-15 (IL-15)-IL-15 receptor α fusion protein, in metastatic melanoma and colorectal cancer, Mol Cancer Ther 2009,8(9).
Chou et al. Effects of immunotherapy of IL-6 and IL-15 plasmids on transmissible venereal tumor in beagles, Veterinary Immunology and Immunopathology 130 (2009) 25-34.
Han et al. TGF-beta signaling and its targeting for glioma treatment, Am J Cancer Res 2015, 5(3):945-955.
Hurton, Tethered IL-15 to Augment the Therapeutic Potential of T Cells Expressing Chimeric Antigen Receptor: Maintaining Memory Potential, Persistence, and Antitumor Activity, (2014). UT GSBS Dissertations and Theses (Open Access). 421.
Hurton et al. Tethered IL-15 augments antitumor activity and promotes a stem-cell memory subset in tumor-specific T cells, Proc Natl Acad Sci U S A. 2016,113(48):E7788-E7797.
Lin et al. Combined immunogene therapy of IL-6 and IL-15 enhances anti-tumor activity through augmented NK cytotoxicity, Cancer Letters 272 (2008) 285-295.

(Continued)

*Primary Examiner* — Bridget E Bunner
*Assistant Examiner* — Fozia Hamud
(74) *Attorney, Agent, or Firm* — Emory Patent Group

(57) ABSTRACT

This disclosure relates to compositions and conjugates comprising an interleukin, e.g., IL-15 and a polypeptide that specifically binds TGF-beta. Typically the polypeptide that specifically binds TGF-beta is a type II TGF-beta receptor. In certain embodiments, the type II TGF-beta receptor is a human isoform, fragment or variant thereof. Uses for treating or preventing cancer and infectious diseases are contemplated.

7 Claims, 5 Drawing Sheets

Specification includes a Sequence Listing.

(56) References Cited

OTHER PUBLICATIONS

Lucas et al. Dysregulation of IL-15-mediated T-cell homeostasis in TGF-beta dominant-negative receptor transgenic mice, Blood. 2006, 108:2789-2795.

Mortier et al. Soluble Interleukin-15 Receptor alpha (IL-15Ralpha)-sushi as a Selective and Potent Agonist of IL-15 Action through IL-15Rbeta/gamma, J Biol Chem. 2006, 281(3):1612-9.

Ng et al. Activation of NK and CD8+ T-Cells with a Novel IL-15 and TGF-beta Receptor Fusion Protein Confers Anti-Tumor Immunity. Blood, 2015, 126:3421.

Ng et al. Novel TGF-beta antagonist and IL-15 fusion protein enhances formation of memory CD8+ T-cells and prevents the formation of regulatory CD4+ T-cells, Cytotherapy, vol. 17, Issue 6, Supplement, Jun. 2015, p. S19.

Ng et al. Stimulation of natural killer cell-mediated tumor immunity by an IL-15/TGF-beta neutralizing fusion protein, Cancer Res. 2016, 76(19): 5683-5695.

Rafei et al. AGMCSF and IL-15 fusokine leads to paradoxical immunosuppression in vivo via asymmetrical JAK/STAT signaling through the IL-15 receptor complex, Blood. 2007,109:2234-2242.

Rafei et al. GIFT15 fusokine to foil immunity's follies, Immunotherapy, 2009, 1(6), 913-915.

Rubinstein et al. Converting IL-15 to a superagonist by binding to soluble IL-15Ralpha, Proc Natl Acad Sci U S A. 2006, 103(24):9166-71.

Sanjabi et al. Opposing effects of TGF-? and IL-15 control the number of short lived effector CD8+ T cells, Immunity. 2009, 31(1): 131-144.

Seay et al. In Vivo Activation of Human NK Cells by Treatment with an Interleukin-15 Superagonist Potently Inhibits Acute In Vivo HIV-1 Infection in Humanized Mice, J Virol, 89:6264-6274, 2015.

Stoklasek et al. Combined IL-15/IL-15Ralpha Immunotherapy Maximizes IL-15 Activity In Vivo, J Immunol. 2006, 177(9): 6072-6080.

Zhang et al. Interleukin-15 combined with an anti-CD40 antibody provides enhanced therapeutic efficacy for murine models of colon cancer, Proc Natl Acad Sci U S A. 2009, 106(18):7513-7518.

Bork et al. Powers and Pitfalls in Sequence Analysis: The 70% Hurdle, Genome Res. 2000, 10: 398-400.

Doerks et al. Protein annotation: detective work for function prediction, TIG, 1998 vol. 14 No. 6, p. 248-250.

Kelley et al. The Phyre2 web portal for protein modeling, prediction and analysis, Nature Protocols, vol. 10, pp. 845-858 (2015).

MacKenzie et al. Tertiary alphabet for the observable protein structural universe, Proceedings of the National Academy of Sciences, 2016, 113 (47) E7438-E7447.

MacKenzie et al. Protein Structural Motifs in Prediction and Design, Curr Opin Struct Biol. 2017, 44: 161-167.

Marks et al. Protein structure prediction from sequence variation, Nat Biotechnol. 2012, 30(11): 1072-1080.

Ng et al. Concise Review: Engineering the Fusion of Cytokines for the Modulation of Immune Cellular Responses in Cancer and Autoimmune Disorders Stem Cells Translational Medicine, 2015, 4:66-73.

Penafuerte et al. Novel TGF-P Antagonist Inhibits Tumor Growth and Angiogenesis by Inducing IL-2 Receptor-Driven STAT1 Activation, J Immunol. 2011, 186(12):6933-6944.

Saldano et al. Evolutionary Conserved Positions Define Protein Conformational Diversity, PLoS Comput Biol, 2016, 12(3): e1004775.

Shihab et al. GTB—an online genome tolerance browser, Shihab et al. BMC Bioinformatics (2017) 18:20.

Skolnick et al. From genes to protein structure and function: novel applications of computational approaches in the genomic era, Trends Biotechnol. 2000, 18(1):34-39.

Tokuriki et al. Stability effects of mutations and protein evolvability, Curr Opin Struct Biol. 2009,19(5):596-604.

Wei et al. Recent Progress in Machine Learning-Based Methods for Protein Fold Recognition, Int. J. Mol. Sci. 2016, 17, 2118, 13 pages.

Wells, Additivity of Mutational Effects in Protein, Biochemistry, 1990, 29(37) 8509-8517.

Extended European Search Report, EP application No. 16808155.2 dated Sep. 25, 2018.

* cited by examiner

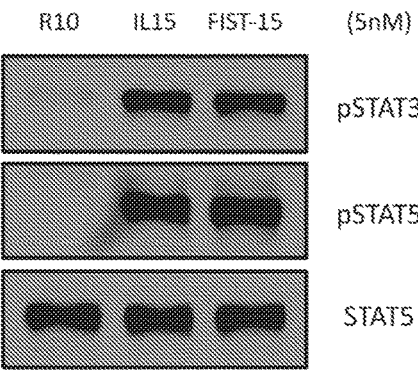
FIG. 1D
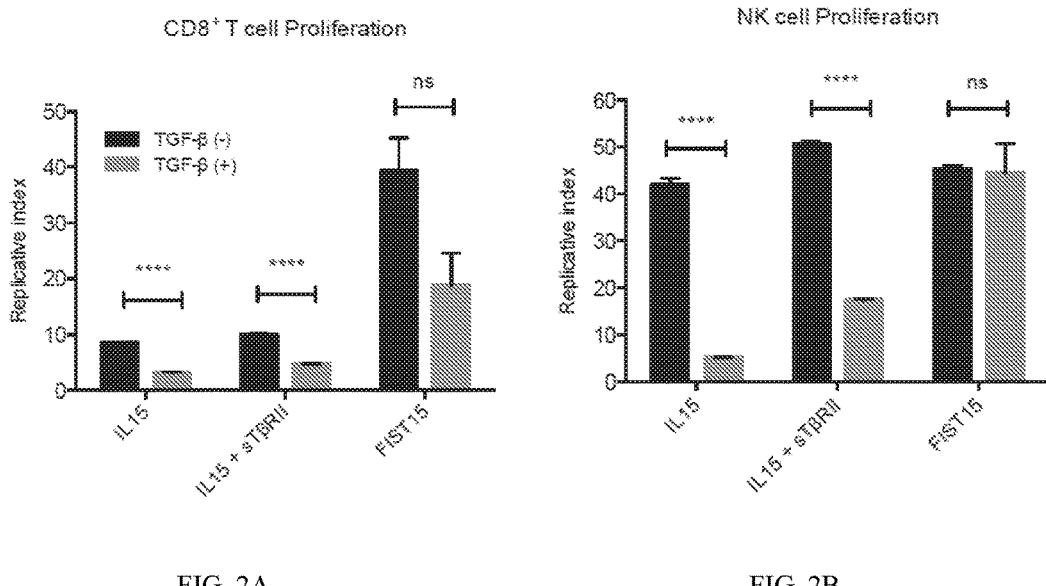
FIG. 2A                                    FIG. 2B

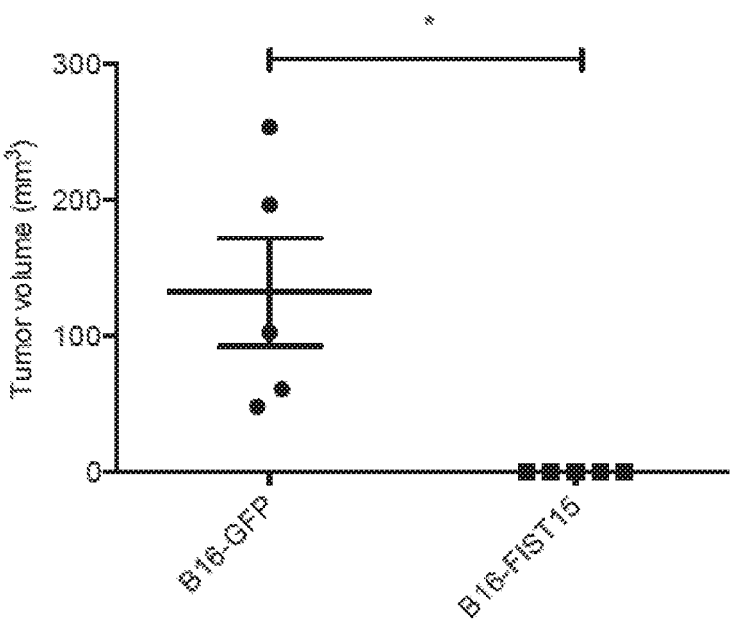
FIG. 3A
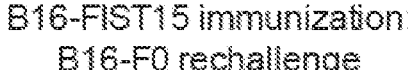
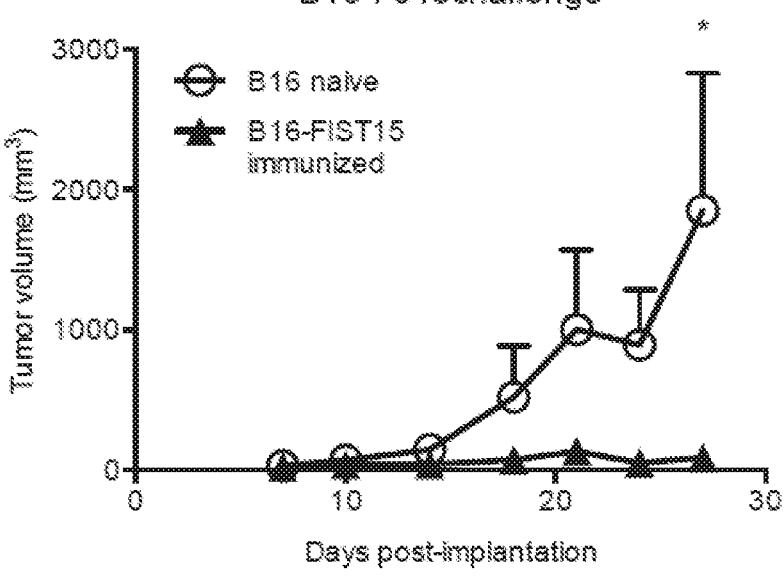
FIG. 3B

SEQUENCE LISTING

```
<160> NUMBER OF SEQ ID NOS: 32

<210> SEQ ID NO 1
<211> LENGTH: 137
<212> TYPE: PRT
<213> ORGANISM: Homo sapiens

<400> SEQUENCE: 1

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
            115                 120                 125

Glu Glu Tyr Asn Thr Ser Asn Pro Asp
    130                 135

<210> SEQ ID NO 2
<211> LENGTH: 114
<212> TYPE: PRT
<213> ORGANISM: Homo sapiens

<400> SEQUENCE: 2

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
```

-continued

```
65                70                75                80

Thr Glu Ser Gly Cys Lys Glu Cys Glu Glu Leu Glu Glu Lys Asn Ile
                 85                90                95

Lys Glu Phe Leu Gln Ser Phe Val His Ile Val Gln Met Phe Ile Asn
                100               105               110

Thr Ser

<210> SEQ ID NO 3
<211> LENGTH: 61
<212> TYPE: PRT
<213> ORGANISM: Artificial
<220> FEATURE:
<223> OTHER INFORMATION: Synthetic

<400> SEQUENCE: 3

Cys Pro Pro Pro Met Ser Val Glu His Ala Asp Ile Trp Val Lys Ser
1               5                 10                15

Tyr Ser Leu Tyr Ser Arg Glu Arg Tyr Ile Cys Asn Ser Gly Phe Lys
                20                25                30

Arg Lys Ala Gly Thr Ser Ser Leu Thr Glu Cys Val Leu Asn Lys Ala
        35                40                45

Thr Asn Val Ala His Trp Thr Thr Pro Ser Leu Lys Cys
        50                55                60

<210> SEQ ID NO 4
<211> LENGTH: 61
<212> TYPE: PRT
<213> ORGANISM: Artificial
<220> FEATURE:
<223> OTHER INFORMATION: Synthetic

<400> SEQUENCE: 4

Cys Pro Pro Pro Val Ser Ile Glu His Ala Asp Ile Arg Val Lys Asn
1               5                 10                15

Tyr Ser Val Asn Ser Arg Glu Arg Tyr Val Cys Asn Ser Gly Phe Lys
                20                25                30

Arg Lys Ala Gly Thr Ser Thr Leu Ile Glu Cys Val Ile Asn Lys Asn
        35                40                45

Thr Asn Val Ala His Trp Thr Thr Pro Ser Leu Lys Cys
        50                55                60

<210> SEQ ID NO 5
<211> LENGTH: 14
<212> TYPE: PRT
<213> ORGANISM: Artificial
<220> FEATURE:
<223> OTHER INFORMATION: Synthetic

<400> SEQUENCE: 5

Ser Gly Gly Thr Ser Gly Ser Thr Ser Gly Thr Gly Ser Thr
1               5                 10

<210> SEQ ID NO 6
<211> LENGTH: 15
<212> TYPE: PRT
<213> ORGANISM: Artificial
<220> FEATURE:
<223> OTHER INFORMATION: Synthetic

<400> SEQUENCE: 6

Ala Gly Ser Ser Thr Gly Ser Ser Thr Gly Pro Gly Ser Thr Thr
1               5                 10                15
```

```
<210> SEQ ID NO 7
<211> LENGTH: 7
<212> TYPE: PRT
<213> ORGANISM: Artificial
<220> FEATURE:
<223> OTHER INFORMATION: Synthetic

<400> SEQUENCE: 7

Gly Gly Ser Gly Gly Ala Pro
1               5

<210> SEQ ID NO 8
<211> LENGTH: 8
<212> TYPE: PRT
<213> ORGANISM: Artificial
<220> FEATURE:
<223> OTHER INFORMATION: Synthetic

<400> SEQUENCE: 8

Gly Gly Gly Val Glu Gly Gly Gly
1               5

<210> SEQ ID NO 9
<211> LENGTH: 7
<212> TYPE: PRT
<213> ORGANISM: Artificial
<220> FEATURE:
<223> OTHER INFORMATION: Synthetic

<400> SEQUENCE: 9

Gly Thr Lys Val His Met Lys
1               5

<210> SEQ ID NO 10
<211> LENGTH: 13
<212> TYPE: PRT
<213> ORGANISM: Artificial
<220> FEATURE:
<223> OTHER INFORMATION: Synthetic

<400> SEQUENCE: 10

Pro Gly Thr Ser Gly Gln Gln Pro Ser Val Gly Gln Gln
1               5                   10

<210> SEQ ID NO 11
<211> LENGTH: 5
<212> TYPE: PRT
<213> ORGANISM: Artificial
<220> FEATURE:
<223> OTHER INFORMATION: Synthetic

<400> SEQUENCE: 11

Gly Thr Ser Gly Gln
1               5

<210> SEQ ID NO 12
<211> LENGTH: 10
<212> TYPE: PRT
<213> ORGANISM: Artificial
<220> FEATURE:
<223> OTHER INFORMATION: Synthetic

<400> SEQUENCE: 12

Pro Lys Pro Ser Thr Pro Pro Gly Ser Ser
1               5                   10
```

```
<210> SEQ ID NO 13
<211> LENGTH: 6
<212> TYPE: PRT
<213> ORGANISM: Artificial
<220> FEATURE:
<223> OTHER INFORMATION: Synthetic

<400> SEQUENCE: 13

Gly Gly Ser Ser Gly Gly
1               5

<210> SEQ ID NO 14
<211> LENGTH: 19
<212> TYPE: PRT
<213> ORGANISM: Artificial
<220> FEATURE:
<223> OTHER INFORMATION: Synthetic

<400> SEQUENCE: 14

Gly Gly Ser Gly Gly Gly Gly Ser Gly Gly Gly Ser Gly Gly Gly Gly
1               5                   10                  15

Ser Leu Gln

<210> SEQ ID NO 15
<211> LENGTH: 5
<212> TYPE: PRT
<213> ORGANISM: Artificial
<220> FEATURE:
<223> OTHER INFORMATION: Synthetic

<400> SEQUENCE: 15

Asp Asp Asp Asp Lys
1               5

<210> SEQ ID NO 16
<211> LENGTH: 5
<212> TYPE: PRT
<213> ORGANISM: Artificial
<220> FEATURE:
<223> OTHER INFORMATION: Synthetic

<400> SEQUENCE: 16

Ile Glu Asp Gly Arg
1               5

<210> SEQ ID NO 17
<211> LENGTH: 6
<212> TYPE: PRT
<213> ORGANISM: Artificial
<220> FEATURE:
<223> OTHER INFORMATION: Synthetic

<400> SEQUENCE: 17

Leu Val Pro Arg Gly Ser
1               5

<210> SEQ ID NO 18
<211> LENGTH: 7
<212> TYPE: PRT
<213> ORGANISM: Artificial
<220> FEATURE:
<223> OTHER INFORMATION: Synthetic

<400> SEQUENCE: 18

Glu Asn Leu Tyr Phe Gln Gly
1               5
```

```
<210> SEQ ID NO 19
<211> LENGTH: 8
<212> TYPE: PRT
<213> ORGANISM: Artificial
<220> FEATURE:
<223> OTHER INFORMATION: Synthetic

<400> SEQUENCE: 19

Leu Glu Val Leu Phe Gln Gly Pro
1               5

<210> SEQ ID NO 20
<211> LENGTH: 5
<212> TYPE: PRT
<213> ORGANISM: Artificial
<220> FEATURE:
<223> OTHER INFORMATION: Synthetic

<400> SEQUENCE: 20

Leu Phe Pro Thr Ser
1               5

<210> SEQ ID NO 21
<211> LENGTH: 355
<212> TYPE: PRT
<213> ORGANISM: Artificial
<220> FEATURE:
<223> OTHER INFORMATION: Synthetic

<400> SEQUENCE: 21

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
            85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Gly Thr Gly Gly Ser Ser Gly
    130                 135                 140

Ile Thr Cys Pro Pro Pro Met Ser Val Glu His Ala Asp Ile Trp Val
145                 150                 155                 160

Lys Ser Tyr Ser Leu Tyr Ser Arg Glu Arg Tyr Ile Cys Asn Ser Gly
                165                 170                 175

Phe Lys Arg Lys Ala Gly Thr Ser Ser Leu Thr Glu Cys Val Leu Asn
            180                 185                 190

Lys Ala Thr Asn Val Ala His Trp Thr Thr Pro Ser Leu Lys Cys Ile
        195                 200                 205

Arg Asp Pro Ala Leu Val His Gln Arg Pro Ala Pro Pro Ser Gly Gly
    210                 215                 220
```

-continued

```
Ser Gly Gly Gly Gly Ser Gly Gly Gly Ser Gly Gly Gly Ser Leu
225             230             235             240

Gln Asn Trp Val Asn Val Ile Ser Asp Leu Lys Lys Ile Glu Asp Leu
            245             250             255

Ile Gln Ser Met His Ile Asp Ala Thr Leu Tyr Thr Glu Ser Asp Val
            260             265             270

His Pro Ser Cys Lys Val Thr Ala Met Lys Cys Phe Leu Leu Glu Leu
            275             280             285

Gln Val Ile Ser Leu Glu Ser Gly Asp Ala Ser Ile His Asp Thr Val
            290             295             300

Glu Asn Leu Ile Ile Leu Ala Asn Asn Ser Leu Ser Ser Asn Gly Asn
305             310             315             320

Val Thr Glu Ser Gly Cys Lys Glu Cys Glu Glu Leu Glu Glu Lys Asn
            325             330             335

Ile Lys Glu Phe Leu Gln Ser Phe Val His Ile Val Gln Met Phe Ile
            340             345             350

Asn Thr Ser
            355

<210> SEQ ID NO 22
<211> LENGTH: 567
<212> TYPE: PRT
<213> ORGANISM: Artificial
<220> FEATURE:
<223> OTHER INFORMATION: Synthetic

<400> SEQUENCE: 22

Met Gly Arg Gly Leu Leu Arg Gly Leu Trp Pro Leu His Ile Val Leu
1               5               10              15

Trp Thr Arg Ile Ala Ser Thr Ile Pro Pro His Val Gln Lys Ser Val
            20              25              30

Asn Asn Asp Met Ile Val Thr Asp Asn Asn Gly Ala Val Lys Phe Pro
            35              40              45

Gln Leu Cys Lys Phe Cys Asp Val Arg Phe Ser Thr Cys Asp Asn Gln
    50              55              60

Lys Ser Cys Met Ser Asn Cys Ser Ile Thr Ser Ile Cys Glu Lys Pro
65              70              75              80

Gln Glu Val Cys Val Ala Val Trp Arg Lys Asn Asp Glu Asn Ile Thr
            85              90              95

Leu Glu Thr Val Cys His Asp Pro Lys Leu Pro Tyr His Asp Phe Ile
            100             105             110

Leu Glu Asp Ala Ala Ser Pro Lys Cys Ile Met Lys Glu Lys Lys Lys
            115             120             125

Pro Gly Glu Thr Phe Phe Met Cys Ser Cys Ser Ser Asp Glu Cys Asn
    130             135             140

Asp Asn Ile Ile Phe Ser Glu Glu Tyr Asn Thr Ser Asn Pro Asp Leu
145             150             155             160

Leu Leu Val Ile Phe Gln Val Thr Gly Ile Ser Leu Leu Pro Pro Leu
            165             170             175

Gly Val Ala Ile Ser Val Ile Ile Ile Phe Tyr Cys Tyr Arg Val Asn
            180             185             190

Arg Gln Gln Lys Leu Ser Ser Thr Trp Glu Thr Gly Lys Thr Arg Lys
            195             200             205

Leu Met Glu Phe Ser Glu His Cys Ala Ile Ile Leu Glu Asp Asp Arg
    210             215             220
```

```
Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
                260                 265                 270

Thr Val Ala Val Lys Ile Phe Pro Tyr Glu Glu Tyr Ala Ser Trp Lys
                275                 280                 285

Thr Glu Lys Asp Ile Phe Ser Asp Ile Asn Leu Lys His Glu Asn Ile
                290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
                340                 345                 350

Ser Leu Ala Arg Gly Ile Ala His Leu His Ser Asp His Thr Pro Cys
                355                 360                 365

Gly Arg Pro Lys Met Pro Ile Val His Arg Asp Leu Lys Ser Ser Asn
                370                 375                 380

Ile Leu Val Lys Asn Asp Leu Thr Cys Cys Leu Cys Asp Phe Gly Leu
385                 390                 395                 400

Ser Leu Arg Leu Asp Pro Thr Leu Ser Val Asp Asp Leu Ala Asn Ser
                405                 410                 415

Gly Gln Val Gly Thr Ala Arg Tyr Met Ala Pro Glu Val Leu Glu Ser
                420                 425                 430

Arg Met Asn Leu Glu Asn Val Glu Ser Phe Lys Gln Thr Asp Val Tyr
                435                 440                 445

Ser Met Ala Leu Val Leu Trp Glu Met Thr Ser Arg Cys Asn Ala Val
                450                 455                 460

Gly Glu Val Lys Asp Tyr Glu Pro Pro Phe Gly Ser Lys Val Arg Glu
465                 470                 475                 480

His Pro Cys Val Glu Ser Met Lys Asp Asn Val Leu Arg Asp Arg Gly
                485                 490                 495

Arg Pro Glu Ile Pro Ser Phe Trp Leu Asn His Gln Gly Ile Gln Met
                500                 505                 510

Val Cys Glu Thr Leu Thr Glu Cys Trp Asp His Asp Pro Glu Ala Arg
                515                 520                 525

Leu Thr Ala Gln Cys Val Ala Glu Arg Phe Ser Glu Leu Glu His Leu
                530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
                565
```

```
<210> SEQ ID NO 23
<211> LENGTH: 162
<212> TYPE: PRT
<213> ORGANISM: Artificial
<220> FEATURE:
<223> OTHER INFORMATION: Synthetic

<400> SEQUENCE: 23

Met Arg Ile Ser Lys Pro His Leu Arg Ser Ile Ser Ile Gln Cys Tyr
1                 5                   10                  15
```

Leu Cys Leu Leu Leu Asn Ser His Phe Leu Thr Glu Ala Gly Ile His
            20                 25                   30

Val Phe Ile Leu Gly Cys Phe Ser Ala Gly Leu Pro Lys Thr Glu Ala
            35                 40                   45

Asn Trp Val Asn Val Ile Ser Asp Leu Lys Lys Ile Glu Asp Leu Ile
      50                 55                 60

Gln Ser Met His Ile Asp Ala Thr Leu Tyr Thr Glu Ser Asp Val His
65                 70                 75                   80

Pro Ser Cys Lys Val Thr Ala Met Lys Cys Phe Leu Leu Glu Leu Gln
            85                 90                   95

Val Ile Ser Leu Glu Ser Gly Asp Ala Ser Ile His Asp Thr Val Glu
           100               105               110

Asn Leu Ile Ile Leu Ala Asn Asn Ser Leu Ser Ser Asn Gly Asn Val
           115               120               125

Thr Glu Ser Gly Cys Lys Glu Cys Glu Glu Leu Glu Glu Lys Asn Ile
           130               135               140

Lys Glu Phe Leu Gln Ser Phe Val His Ile Val Gln Met Phe Ile Asn
145                 150                 155                   160

Thr Ser

<210> SEQ ID NO 24
<211> LENGTH: 506
<212> TYPE: PRT
<213> ORGANISM: Artificial
<220> FEATURE:
<223> OTHER INFORMATION: Synthetic

<400> SEQUENCE: 24

His His His His His His His His Glu Asn Leu Tyr Phe Gln Gly Ser
1                5                 10               15

Ile Pro Pro His Val Pro Lys Ser Val Asn Ser Asp Val Met Ala Ser
            20                 25                   30

Asp Asn Gly Gly Ala Val Lys Leu Pro Gln Leu Cys Lys Phe Cys Asp
           35               40               45

Val Arg Leu Ser Thr Cys Asp Asn Gln Lys Ser Cys Met Ser Asn Cys
      50                 55                 60

Ser Ile Thr Ala Ile Cys Glu Lys Pro His Glu Val Cys Val Ala Val
65                 70                 75                   80

Trp Arg Lys Asn Asp Lys Asn Ile Thr Leu Glu Thr Val Cys His Asp
            85                 90                   95

Pro Lys Leu Thr Tyr His Gly Phe Thr Leu Glu Asp Ala Ala Ser Pro
           100               105               110

Lys Cys Val Met Lys Glu Lys Lys Arg Ala Gly Glu Thr Phe Phe Met
           115               120               125

Cys Ala Cys Asn Met Glu Glu Cys Asn Asp Tyr Ile Ile Phe Ser Glu
           130               135               140

Glu Tyr Thr Thr Ser Ser Pro Asp Ile Pro Pro His Val Pro Lys Ser
145                 150                 155                   160

Val Asn Ser Asp Val Met Ala Ser Asp Asn Gly Gly Ala Val Lys Leu
            165                 170               175

Pro Gln Leu Cys Lys Phe Cys Asp Val Arg Leu Ser Thr Cys Asp Asn
           180               185               190

Gln Lys Ser Cys Met Ser Asn Cys Ser Ile Thr Ala Ile Cys Glu Lys
           195               200               205

Pro His Glu Val Cys Val Ala Val Trp Arg Lys Asn Asp Lys Asn Ile

-continued

```
          210             215             220

Thr Leu Glu Thr Val Cys His Asp Pro Lys Leu Thr Tyr His Gly Phe
225                 230             235                 240

Thr Leu Glu Asp Ala Ala Ser Pro Lys Cys Val Met Lys Glu Lys Lys
                245             250             255

Arg Ala Gly Glu Thr Phe Phe Met Cys Ala Cys Asn Met Glu Glu Cys
                260             265             270

Asn Asp Tyr Ile Ile Phe Ser Glu Glu Tyr Thr Thr Ser Ser Pro Asp
                275             280             285

Gly Thr Gly Gly Ser Ser Gly Gly Thr Thr Cys Pro Pro Pro Val Ser
                290             295             300

Ile Glu His Ala Asp Ile Arg Val Lys Asn Tyr Ser Val Asn Ser Arg
305                 310             315                 320

Glu Arg Tyr Val Cys Asn Ser Gly Phe Lys Arg Lys Ala Gly Thr Ser
                325             330             335

Thr Leu Ile Glu Cys Val Ile Asn Lys Asn Thr Asn Val Ala His Trp
                340             345             350

Thr Thr Pro Ser Leu Lys Cys Ile Arg Asp Pro Ser Leu Ala His Tyr
                355             360             365

Ser Pro Val Pro Ser Gly Gly Ser Gly Gly Gly Ser Gly Gly Gly
                370             375             380

Ser Gly Gly Gly Gly Ser Leu Gln Asn Trp Ile Asp Val Arg Tyr Asp
385                 390             395                 400

Leu Glu Lys Ile Glu Ser Leu Ile Gln Ser Ile His Ile Asp Thr Thr
                405             410             415

Leu Tyr Thr Asp Ser Asp Phe His Pro Ser Cys Lys Val Thr Ala Met
                420             425             430

Asn Cys Phe Leu Leu Glu Leu Gln Val Ile Leu His Glu Tyr Ser Asn
                435             440             445

Met Thr Leu Asn Glu Thr Val Arg Asn Val Leu Tyr Leu Ala Asn Ser
450                 455             460

Thr Leu Ser Ser Asn Lys Asn Val Ala Glu Ser Gly Cys Lys Glu Cys
465                 470             475             480

Glu Glu Leu Glu Glu Lys Thr Phe Thr Glu Phe Leu Gln Ser Phe Ile
                485             490             495

Arg Ile Val Gln Met Phe Ile Asn Thr Ser
                500             505
```

```
<210> SEQ ID NO 25
<211> LENGTH: 531
<212> TYPE: PRT
<213> ORGANISM: Artificial
<220> FEATURE:
<223> OTHER INFORMATION: Synthetic

<400> SEQUENCE: 25

Met Asn Phe Leu Leu Ser Trp Val His Trp Ser Leu Ala Leu Leu Leu
1               5               10                  15

Tyr Leu His His Ala Lys Trp Ser Gln Ala Glu Asn Leu Tyr Phe Gln
                20              25              30

Ser His His His His His His His Ile Pro Pro His Val Pro Lys
            35              40              45

Ser Val Asn Ser Asp Val Met Ala Ser Asp Asn Gly Gly Ala Val Lys
        50              55              60

Leu Pro Gln Leu Cys Lys Phe Cys Asp Val Arg Leu Ser Thr Cys Asp
```

56

-continued

```
65              70              75              80

Asn Gln Lys Ser Cys Met Ser Asn Cys Ser Ile Thr Ala Ile Cys Glu
            85              90              95

Lys Pro His Glu Val Cys Val Ala Val Trp Arg Lys Asn Asp Lys Asn
            100             105             110

Ile Thr Leu Glu Thr Val Cys His Asp Pro Lys Leu Thr Tyr His Gly
            115             120             125

Phe Thr Leu Glu Asp Ala Ala Ser Pro Lys Cys Val Met Lys Glu Lys
    130             135             140

Lys Arg Ala Gly Glu Thr Phe Phe Met Cys Ala Cys Asn Met Glu Glu
145             150             155             160

Cys Asn Asp Tyr Ile Ile Phe Ser Glu Glu Tyr Thr Thr Ser Ser Pro
                165             170             175

Asp Ile Pro Pro His Val Pro Lys Ser Val Asn Ser Asp Val Met Ala
            180             185             190

Ser Asp Asn Gly Gly Ala Val Lys Leu Pro Gln Leu Cys Lys Phe Cys
            195             200             205

Asp Val Arg Leu Ser Thr Cys Asp Asn Gln Lys Ser Cys Met Ser Asn
    210             215             220

Cys Ser Ile Thr Ala Ile Cys Glu Lys Pro His Glu Val Cys Val Ala
225             230             235             240

Val Trp Arg Lys Asn Asp Lys Asn Ile Thr Leu Glu Thr Val Cys His
                245             250             255

Asp Pro Lys Leu Thr Tyr His Gly Phe Thr Leu Glu Asp Ala Ala Ser
            260             265             270

Pro Lys Cys Val Met Lys Glu Lys Lys Arg Ala Gly Glu Thr Phe Phe
            275             280             285

Met Cys Ala Cys Asn Met Glu Glu Cys Asn Asp Tyr Ile Ile Phe Ser
    290             295             300

Glu Glu Tyr Thr Thr Ser Ser Pro Asp Gly Thr Gly Gly Ser Ser Gly
305             310             315             320

Gly Thr Thr Cys Pro Pro Pro Val Ser Ile Glu His Ala Asp Ile Arg
                325             330             335

Val Lys Asn Tyr Ser Val Asn Ser Arg Glu Arg Tyr Val Cys Asn Ser
            340             345             350

Gly Phe Lys Arg Lys Ala Gly Thr Ser Thr Leu Ile Glu Cys Val Ile
            355             360             365

Asn Lys Asn Thr Asn Val Ala His Trp Thr Thr Pro Ser Leu Lys Cys
    370             375             380

Ile Arg Asp Pro Ser Leu Ala His Tyr Ser Pro Val Pro Ser Gly Gly
385             390             395             400

Ser Gly Gly Gly Gly Ser Gly Gly Gly Ser Gly Gly Gly Gly Ser Leu
            405             410             415

Gln Asn Trp Ile Asp Val Arg Tyr Asp Leu Glu Lys Ile Glu Ser Leu
            420             425             430

Ile Gln Ser Ile His Ile Asp Thr Thr Leu Tyr Thr Asp Ser Asp Phe
            435             440             445

His Pro Ser Cys Lys Val Thr Ala Met Asn Cys Phe Leu Leu Glu Leu
    450             455             460

Gln Val Ile Leu His Glu Tyr Ser Asn Met Thr Leu Asn Glu Thr Val
465             470             475             480

Arg Asn Val Leu Tyr Leu Ala Asn Ser Thr Leu Ser Ser Asn Lys Asn
            485             490             495
```

-continued

```
Val Ala Glu Ser Gly Cys Lys Glu Cys Glu Glu Leu Glu Glu Lys Thr
        500                 505                 510

Phe Thr Glu Phe Leu Gln Ser Phe Ile Arg Ile Val Gln Met Phe Ile
        515                 520                 525

Asn Thr Ser
    530

<210> SEQ ID NO 26
<211> LENGTH: 508
<212> TYPE: PRT
<213> ORGANISM: Artificial
<220> FEATURE:
<223> OTHER INFORMATION: Synthetic

<400> SEQUENCE: 26

His His His His His His His His Glu Asn Leu Tyr Phe Gln Gly Ser
1               5                   10                  15

Thr Ile Pro Pro His Val Gln Lys Ser Val Asn Asn Asp Met Ile Val
        20                  25                  30

Thr Asp Asn Asn Gly Ala Val Lys Phe Pro Gln Leu Cys Lys Phe Cys
        35                  40                  45

Asp Val Arg Phe Ser Thr Cys Asp Asn Gln Lys Ser Cys Met Ser Asn
    50                  55                  60

Cys Ser Ile Thr Ser Ile Cys Glu Lys Pro Gln Glu Val Cys Val Ala
65                  70                  75                  80

Val Trp Arg Lys Asn Asp Glu Asn Ile Thr Leu Glu Thr Val Cys His
                85                  90                  95

Asp Pro Lys Leu Pro Tyr His Asp Phe Ile Leu Glu Asp Ala Ala Ser
            100                 105                 110

Pro Lys Cys Ile Met Lys Glu Lys Lys Pro Gly Glu Thr Phe Phe
        115                 120                 125

Met Cys Ser Cys Ser Ser Asp Glu Cys Asn Asp Asn Ile Ile Phe Ser
    130                 135                 140

Glu Glu Tyr Asn Thr Ser Asn Pro Asp Thr Ile Pro Pro His Val Gln
145                 150                 155                 160

Lys Ser Val Asn Asn Asp Met Ile Val Thr Asp Asn Asn Gly Ala Val
                165                 170                 175

Lys Phe Pro Gln Leu Cys Lys Phe Cys Asp Val Arg Phe Ser Thr Cys
            180                 185                 190

Asp Asn Gln Lys Ser Cys Met Ser Asn Cys Ser Ile Thr Ser Ile Cys
            195                 200                 205

Glu Lys Pro Gln Glu Val Cys Val Ala Val Trp Arg Lys Asn Asp Glu
    210                 215                 220

Asn Ile Thr Leu Glu Thr Val Cys His Asp Pro Lys Leu Pro Tyr His
225                 230                 235                 240

Asp Phe Ile Leu Glu Asp Ala Ala Ser Pro Lys Cys Ile Met Lys Glu
            245                 250                 255

Lys Lys Lys Pro Gly Glu Thr Phe Phe Met Cys Ser Cys Ser Ser Asp
            260                 265                 270

Glu Cys Asn Asp Asn Ile Ile Phe Ser Glu Glu Tyr Asn Thr Ser Asn
        275                 280                 285

Pro Asp Gly Thr Gly Gly Ser Ser Gly Ile Thr Cys Pro Pro Pro Met
    290                 295                 300

Ser Val Glu His Ala Asp Ile Trp Val Lys Ser Tyr Ser Leu Tyr Ser
305                 310                 315                 320
```

-continued

```
Arg Glu Arg Tyr Ile Cys Asn Ser Gly Phe Lys Arg Lys Ala Gly Thr
                325             330             335

Ser Ser Leu Thr Glu Cys Val Leu Asn Lys Ala Thr Asn Val Ala His
            340             345             350

Trp Thr Thr Pro Ser Leu Lys Cys Ile Arg Asp Pro Ala Leu Val His
        355             360             365

Gln Arg Pro Ala Pro Pro Ser Gly Gly Ser Gly Gly Gly Gly Ser Gly
    370             375             380

Gly Gly Ser Gly Gly Gly Gly Ser Leu Gln Asn Trp Val Asn Val Ile
385             390             395             400

Ser Asp Leu Lys Lys Ile Glu Asp Leu Ile Gln Ser Met His Ile Asp
                405             410             415

Ala Thr Leu Tyr Thr Glu Ser Asp Val His Pro Ser Cys Lys Val Thr
            420             425             430

Ala Met Lys Cys Phe Leu Leu Glu Leu Gln Val Ile Ser Leu Glu Ser
            435             440             445

Gly Asp Ala Ser Ile His Asp Thr Val Glu Asn Leu Ile Ile Leu Ala
    450             455             460

Asn Asn Ser Leu Ser Ser Asn Gly Asn Val Thr Glu Ser Gly Cys Lys
465             470             475             480

Glu Cys Glu Glu Leu Glu Glu Lys Asn Ile Lys Glu Phe Leu Gln Ser
            485             490             495

Phe Val His Ile Val Gln Met Phe Ile Asn Thr Ser
            500             505
```

```
<210> SEQ ID NO 27
<211> LENGTH: 492
<212> TYPE: PRT
<213> ORGANISM: Artificial
<220> FEATURE:
<223> OTHER INFORMATION: Synthetic

<400> SEQUENCE: 27
```

```
Thr Ile Pro Pro His Val Gln Lys Ser Val Asn Asn Asp Met Ile Val
1               5               10              15

Thr Asp Asn Asn Gly Ala Val Lys Phe Pro Gln Leu Cys Lys Phe Cys
            20              25              30

Asp Val Arg Phe Ser Thr Cys Asp Asn Gln Lys Ser Cys Met Ser Asn
            35              40              45

Cys Ser Ile Thr Ser Ile Cys Glu Lys Pro Gln Glu Val Cys Val Ala
    50              55              60

Val Trp Arg Lys Asn Asp Glu Asn Ile Thr Leu Glu Thr Val Cys His
65              70              75              80

Asp Pro Lys Leu Pro Tyr His Asp Phe Ile Leu Glu Asp Ala Ala Ser
                85              90              95

Pro Lys Cys Ile Met Lys Glu Lys Lys Lys Pro Gly Glu Thr Phe Phe
            100             105             110

Met Cys Ser Cys Ser Ser Asp Glu Cys Asn Asp Asn Ile Ile Phe Ser
            115             120             125

Glu Glu Tyr Asn Thr Ser Asn Pro Asp Thr Ile Pro Pro His Val Gln
    130             135             140

Lys Ser Val Asn Asn Asp Met Ile Val Thr Asp Asn Asn Gly Ala Val
145             150             155             160

Lys Phe Pro Gln Leu Cys Lys Phe Cys Asp Val Arg Phe Ser Thr Cys
            165             170             175
```

-continued

```
Asp Asn Gln Lys Ser Cys Met Ser Asn Cys Ser Ile Thr Ser Ile Cys
            180                 185             190

Glu Lys Pro Gln Glu Val Cys Val Ala Val Trp Arg Lys Asn Asp Glu
            195                 200             205

Asn Ile Thr Leu Glu Thr Val Cys His Asp Pro Lys Leu Pro Tyr His
            210                 215             220

Asp Phe Ile Leu Glu Asp Ala Ala Ser Pro Lys Cys Ile Met Lys Glu
225                 230                 235                 240

Lys Lys Lys Pro Gly Glu Thr Phe Phe Met Cys Ser Cys Ser Ser Asp
            245                 250             255

Glu Cys Asn Asp Asn Ile Ile Phe Ser Glu Glu Tyr Asn Thr Ser Asn
            260                 265             270

Pro Asp Gly Thr Gly Gly Ser Ser Gly Ile Thr Cys Pro Pro Pro Met
            275                 280             285

Ser Val Glu His Ala Asp Ile Trp Val Lys Ser Tyr Ser Leu Tyr Ser
            290                 295             300

Arg Glu Arg Tyr Ile Cys Asn Ser Gly Phe Lys Arg Lys Ala Gly Thr
305                 310                 315                 320

Ser Ser Leu Thr Glu Cys Val Leu Asn Lys Ala Thr Asn Val Ala His
            325                 330             335

Trp Thr Thr Pro Ser Leu Lys Cys Ile Arg Asp Pro Ala Leu Val His
            340                 345             350

Gln Arg Pro Ala Pro Pro Ser Gly Gly Ser Gly Gly Gly Ser Gly
            355                 360             365

Gly Gly Ser Gly Gly Gly Gly Ser Leu Gln Asn Trp Val Asn Val Ile
            370                 375             380

Ser Asp Leu Lys Lys Ile Glu Asp Leu Ile Gln Ser Met His Ile Asp
385                 390                 395                 400

Ala Thr Leu Tyr Thr Glu Ser Asp Val His Pro Ser Cys Lys Val Thr
                405                 410             415

Ala Met Lys Cys Phe Leu Leu Glu Leu Gln Val Ile Ser Leu Glu Ser
            420                 425             430

Gly Asp Ala Ser Ile His Asp Thr Val Glu Asn Leu Ile Ile Leu Ala
            435                 440             445

Asn Asn Ser Leu Ser Ser Asn Gly Asn Val Thr Glu Ser Gly Cys Lys
            450                 455             460

Glu Cys Glu Glu Leu Glu Glu Lys Asn Ile Lys Glu Phe Leu Gln Ser
465                 470                 475             480

Phe Val His Ile Val Gln Met Phe Ile Asn Thr Ser
                485                 490
```

<210> SEQ ID NO 28
<211> LENGTH: 26
<212> TYPE: PRT
<213> ORGANISM: Artificial
<220> FEATURE:
<223> OTHER INFORMATION: Synthetic

<400> SEQUENCE: 28

```
Met Asn Phe Leu Leu Ser Trp Val His Trp Ser Leu Ala Leu Leu Leu
1               5               10                  15

Tyr Leu His His Ala Lys Trp Ser Gln Ala
            20                  25
```

<210> SEQ ID NO 29

-continued

```
<211> LENGTH: 6
<212> TYPE: PRT
<213> ORGANISM: Artificial
<220> FEATURE:
<223> OTHER INFORMATION: Synthetic

<400> SEQUENCE: 29

Gly Gly Gly Gly Gly Gly
1               5

<210> SEQ ID NO 30
<211> LENGTH: 5
<212> TYPE: PRT
<213> ORGANISM: Artificial
<220> FEATURE:
<223> OTHER INFORMATION: Synthetic

<400> SEQUENCE: 30

Gly Gly Gly Gly Thr
1               5

<210> SEQ ID NO 31
<211> LENGTH: 6
<212> TYPE: PRT
<213> ORGANISM: Artificial
<220> FEATURE:
<223> OTHER INFORMATION: Synthetic

<400> SEQUENCE: 31

Gly Gly Gly Pro Pro Pro
1               5

<210> SEQ ID NO 32
<211> LENGTH: 7
<212> TYPE: PRT
<213> ORGANISM: Artificial
<220> FEATURE:
<223> OTHER INFORMATION: Synthetic

<400> SEQUENCE: 32

Gly Gly Gly Ala Pro Pro Pro
1               5
```

COMPOSITIONS AND CONJUGATES COMPRISING AN INTERLEUKIN AND POLYPEPTIDES THAT SPECIFICALLY BIND TGF-BETA

CROSS-REFERENCE TO RELATED APPLICATIONS

This application is the National Stage of International Application No. PCT/US2016/036358 filed Jun. 8, 2016, which claims the benefit of priority to U.S. Provisional Application No. 62/173,592 filed Jun. 10, 2015. The entirety of each of these applications are hereby incorporated by reference for all purposes.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 15107US-updated_ST25.txt. The text file is 35 KB, was created on Apr. 2, 2019, and is being submitted electronically via EFS-Web.

BACKGROUND

Interleukins are protein based signaling molecules that typically participate in immune responses through stimulation of corresponding cells. For example, interleukin 15 (IL-15) is a cytokine that is able to activate NK cells and memory T-cells. Due to the stimulant properties of the immune system, this interleukin has anti-tumoral properties. Bessard et al. report antitumor activity of a fusion protein of IL-15 and IL-15 receptor α in metastatic melanoma and colorectal cancer. Mol Cancer Ther, 2009, 8; 2736. See also Rubinstein et al., 2006, Proc Natl Acad Sci USA, 103:9166-71 and Stoklasek et al., 2006, J Immunol, 177:6072-80. IL-15 has been used in anti-tumoral therapy in combination with other treatments such as anti-CD40, IL-7 or IL-6 antibodies. See Chou et al., 2009, Vet Immunol Immunopathol, 130:25-34; Lin et al., Cancer Lett, 2008, 272(2):285-95; and Zhang et al., Proc Natl Acad Sci USA, 2009, 106:7513-8. IL-15 is also involved in protection against viral infections.

Mortier et al. report interleukin-15 receptor alpha (IL-15R alpha)-sushi is an agonist of IL-15. J Biol Chem, 2006, 281(3):1612-9.

Lopez et al. report compositions comprising apolipoprotein A polypeptide and interleukin 15. See U.S. Pat. No. 8,771,664.

References cited herein are not an admission of prior art.

SUMMARY

This disclosure relates to compositions and conjugates comprising an interleukin, e.g., IL-15 and a polypeptide that specifically binds TGF-beta. Typically the polypeptide that specifically binds TGF-beta is a type II TGF-beta receptor. In certain embodiments, the type II TGF-beta receptor is a human isoform, fragment or variant thereof. Uses for treating or preventing cancer and infectious diseases are contemplated.

In certain embodiments, the type II TGF-beta receptor is a human isoform, fragment or variant thereof, e.g., has greater than 50% sequence identity or similarity to TIP-PHVQKSVNNDMIVTDNNGAVKFPQLCKFCDVRF-STCDNQKSCMSNCSITSICEKPQE VCVAVWRKNDEN-ITLETVCHDPKLPYHDFILEDAASPKCIMKEKKK-PGETFFMCSCSSD ECNDNIIFSEEYNTSNPD SEQ ID NO: 1.

In certain embodiments, the IL-15 is a human isoform, fragment or variant thereof, e.g., has greater than 50% sequences identity or similarity to NWVNVISDLK-KIEDLIQSMHIDATLYTESDVHPSCKVTAMKCFL-LELQVISLESGDASIH DTVENLIILANNSLSSNG-NVTESGCKECEELEEKNIKEFLQSFVHIVQMFINTS (SEQ ID NO:2).

In certain embodiments, the conjugate further comprises a sushi domain of the IL-15 receptor alpha chain, e.g., has greater than 50% sequences identity or similarity to CPPPMSVEHADIWVKSYSLYSRERYICNSGFKRK-AGTSSLTECVLNKATNVAHWTTPSL KC (SEQ ID NO: 3).

In certain embodiments, the conjugate comprises a polypeptide having greater than 50, 60, 70, 80, 90, 95, or 98% sequences identity or similarity to TIPPHVQKSVNND-MIVTDNNGAVKFPQLCKFCDVRF-STCDNQKSCMSNCSITSICEKPQE VCVAVWRKNDEN-ITLETVCHDPKLPYHDFILEDAASPKCIMKEKKKPG-ETFFMCSCSSD ECNDNIIF-SEEYNTSNPDGTGGSSGITCPPPMSVEHADIWVK-SYSLYSRERYICNSGFKRK AGTSSLTECVLNKATN-VAHWTTPSLKCIRDPALVHQRPAPPSGGSGGGGS-GGGSGGGGS LQNWVNVISDLKKIEDLIQSMHIDAT-LYTESDVHPSCKVTAMKCFLLELQVISLESGDASI HDTVENLIILANNSLSSNGNVTESGCKECEELEEKNI-KEFLQSFVHIVQMFINTS (SEQ ID NO: 21) or TIPPHVQKSVNNDMIVTDNN-GAVKFPQLCKFCDVRFSTCDNQKSCMSNCSITSIC EKPQEVCVAVWRKNDENITLETVCHDPKLPYHD-FILEDAASPKCIMKEKKKPGETFFMC SCSSDECND-NIIFSEEYNTSNPDTIPPHVQKSVNNDMIVTDNN-GAVKFPQLCKFCDVRFS TCDNQKSCMSNCSITSICEKPQEVCVAVWRKNDEN-ITLETVCHDPKLPYHDFILEDAASP KCI-MKEKKKPGETFFMCSCSSDECNDNIIF-SEEYNTSNPDGTGGSSGITCPPPMSVEHADI WVKSYSLYSRERYICNSGFKRK-AGTSSLTECVLNKATNVAHWTTPSLKCIRDPALVHQR PAPPSGGSGGGGSGGGSGGGGSLQNWVNVISDLK-KIEDLIQSMHIDATLYTESDVHPSC KVTAMKCFL-LELQVISLESGDASIHDTVENLIILANNSLSSNG-NVTESGCKECEELEEKNI KEFLQSFVHIVQMFINTS (SEQ ID NO: 27).

In certain embodiments, the disclosure relates to polynucleotides encoding conjugates or components disclosed herein. In certain embodiments, the disclosure relates to vectors comprising polynucleotides disclosed herein. In certain embodiments, the disclosure relates to expression system comprising vectors disclosed herein.

In certain embodiments, the disclosure relates to methods of treating or preventing cancer or infectious diseases comprising administering an effective amount of compositions or conjugates disclosed herein to a subject in need thereof.

In certain embodiments, the disclosure relates to methods of treating or preventing cancer comprising isolating immune modulatory cells, such as, NK, T-cells, or B-cells, e.g., from a subject, mixing the cells with compositions or conjugates disclosed herein under conditions such that the cells proliferate and/or become activated and re-administering the cells or replicated versions thereof to a subject in need thereof.

In certain embodiments, the disclosure relates to methods of treating cancer comprising isolating lymphoid cells from a subject or from a random donor, mixing the cells with a conjugate disclosed herein under conditions such that the cells proliferate and/or become activated and administering an effective amount of the cells or cells derived therefrom to a subject in need thereof. In certain embodiments, the lymphoid cells are T-cells, NK and/or B-cells optionally genetically engineered to express other proteins, fusions or chimeric antigen receptors.

In certain embodiments, the cancer is a lymphoma, melanoma, hepatocellular carcinoma, colorectal cancer (CRC), castration-resistant prostate cancer (CRPC), non-small-cell lung cancer (NSCLC) and renal cell carcinoma (RCC).

In certain embodiments, the methods further comprise administering the conjugate in combination with immune checkpoint inhibitors/blockading agents, immunostimulatory cytokines, GM-CSF, anti-PD-1, anti-PD-L1, anti-CTLA-4, anti-CD40, anti-IL-7, or anti-IL-6 antibodies or combinations thereof.

In certain embodiments, the anti-CTLA-4 antibody is ipilimumab, the anti-PD-1 antibody is selected from nivolumab, pembrolizumab, and pidilizumab, and the anti-PD-L1 is selected from (MDX-1105) BMS-936559, MPDL3280A (atezolizumab), MEDI4736 (durvalumab), and MSB0010718C.

In certain embodiments, the methods further comprise administering the conjugate in combination with bevacizumab, erlotinib, ipilimumab, bevacizumab and erlotinib, bevacizumab and erlotinib, lambrolizumab, dasatinib, IL-2, pembrolizumab, cisplatin and pemetrexed, carboplatin and paclitaxel, pegylated IFN-$\alpha$2b, axitinib, lenalidomide and dexamethasone, trametinib and dabrafenib, and IFN-$\gamma$.

In certain embodiments, the disclosure relates to uses of compositions and conjugates disclosed herein for the production of a medicament, e.g., a medicament used to treat or prevent diseases and conditions reported herein.

BRIEF DESCRIPTION OF THE FIGURES

FIG. 1D shows data on STAT phosphorylation.

FIG. 2A shows data indicating FIST15 induces CD8+ T cell proliferation in the presence of TGF-$\beta$1. Murine splenocytes labeled with CF SE were cultured with IL15, IL15+sT$\beta$RII, or FIST15 (500 pM) in the presence or absence of TGF-$\beta$1 (5 ng/ml) for 72 hours before flow cytometric analysis. The replicative index of representing fold-expansion±SEM of responding cells (n=3 experiments) is shown in (B).

FIG. 2B shows data for NK cell proliferation.

FIG. 3A shows a graph of tumor volumes at day 10 post-implantation. Locoregional secretion of FIST15 by B16-F0 melanoma prevents tumor establishment by activating NK cells in vivo. 1×10⁶B16-F0 transduced with FIST15 (B16-FIST15) or a vector containing GFP (B16-GFP) cells were implanted subcutaneously into the flank of immunocompetent C57Bl/6 mice (n=5, each) and monitored for tumor growth.

FIG. 3B shows a graph of tumor volumes where mice that had received B16-FIST15 (n=5) were rechallenged with B16-F0 cells compared to naïve mice (B16-naïve; n=3) and monitored for tumor growth.

DETAILED DESCRIPTION

Figure 1A:
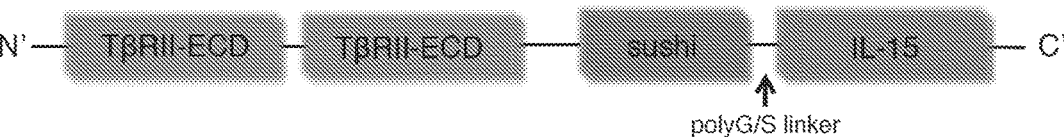
FIG. 1A illustrates an embodiment of the disclosure, FIST-15.
Figure 1B:
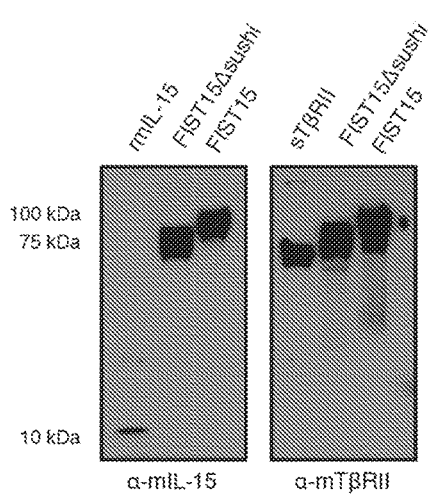
FIG. 1B shows immunoblots of variant FIST-15s.
Figure 1C:
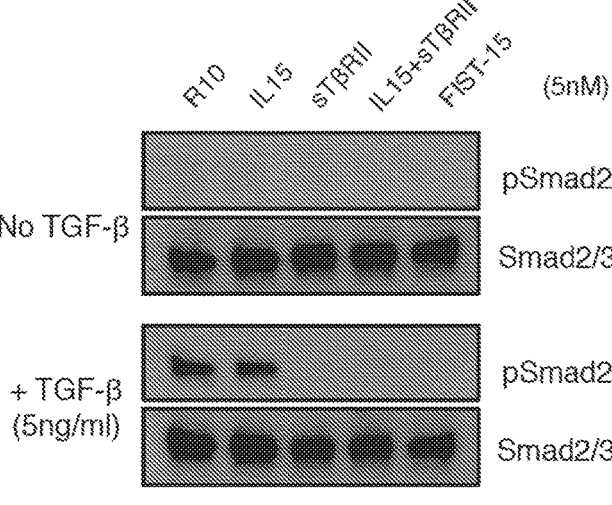
FIG. 1C shows data indicating the ability to neutralize TGF-beta mediated Smad signaling.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

As used herein, the term "conjugate" refers to molecular entities joined by covalent bonds or other arrangement that provides substantially irreversible binding under physiological conditions. For example, two proteins, isolated and/or purified polypeptide sequence, may be conjugated together by a linker polymer, e.g., amino acid, polypeptide sequence, ethylene glycol polymer. Two proteins may be conjugated together by linking one protein to a ligand and linking the second protein to a receptor, e.g., streptavidin and biotin or an antibody and an epitope.

As used herein, the term "combination with" when used to describe administration with an additional treatment means that the agent may be administered prior to, together with, or after the additional treatment, or a combination thereof.

As used herein, "subject" refers to any animal, typically a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

As used herein, "amino acid sequence" refers to an amino acid sequence of a protein molecule. An "amino acid sequence" can be deduced from the nucleic acid sequence encoding the protein. However, terms such as "polypeptide" or "protein" are not meant to limit the amino acid sequence to the deduced amino acid sequence, but include non-naturally occurring amino acids, post-translational modifications of the deduced amino acid sequences, such as amino acid deletions, additions, and modifications such as glycosylation and addition of lipid moieties.

The term "a polynucleotide sequence encoding" a specified polypeptide refers to a nucleic acid sequence comprising the coding region of a gene or in other words the nucleic acid sequence which encodes a gene product. The coding region may be present in a cDNA, genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present disclosure may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro (cell free) systems. Systems for recombinant protein expression typically utilize cells transfecting with a DNA expression vector that contains the template. The cells are cultured under conditions such that they translate the desired protein. Expressed proteins are extracted for subsequent purification. In vivo protein expression systems using prokaryotic and eukaryotic cells are well known. Also, some proteins are recovered using denaturants and protein-refolding procedures. In vitro (cell-free) protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vectors, these extracts and components can synthesize proteins of interest. Cell-free systems typically do not contain proteases and enable labeling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

A "selectable marker" is a nucleic acid introduced into a recombinant vector that encodes a polypeptide that confers a trait suitable for artificial selection or identification (report gene), e.g., beta-lactamase confers antibiotic resistance, which allows an organism expressing beta-lactamase to survive in the presence antibiotic in a growth medium. Another example is thymidine kinase, which makes the host sensitive to ganciclovir selection. It may be a screenable marker that allows one to distinguish between wanted and unwanted cells based on the presence or absence of an expected color. For example, the lac-z-gene produces a beta-galactosidase enzyme which confers a blue color in the presence of X-gal (5-bromo-4-chloro-3-indolyl-(3-D-galactoside). If recombinant insertion inactivates the lac-z-gene, then the resulting colonies are colorless. There may be one or more selectable markers, e.g., an enzyme that can complement to the inability of an expression organism to synthesize a particular compound required for its growth (auxotrophic) and one able to convert a compound to another that is toxic for growth. URA3, an orotidine-5' phosphate decarboxylase, is necessary for uracil biosynthesis and can complement ura3 mutants that are auxotrophic for uracil. URA3 also converts 5-fluoroorotic acid into the toxic compound 5-fluorouracil. Additional contemplated selectable markers include any genes that impart antibacterial resistance or express a fluorescent protein. Examples include, but are not limited to, the following genes: ampr, camr, tetr, blasticidinr, neor, hygr, abxr, neomycin phosphotransferase type II gene (nptII), p-glucuronidase (gus), green fluorescent protein (gfp), egfp, yfp, mCherry, p-galactosidase (lacZ), lacZa, lacZAM15, chloramphenicol acetyltransferase (cat), alkaline phosphatase (phoA), bacterial luciferase (luxAB), bialaphos resistance gene (bar), phosphomannose isomerase (pmi), xylose isomerase (xylA), arabitol dehydrogenase (atlD), UDP-glucose:galactose-1-phosphate uridyltransferasel (galT), feedback-insensitive α subunit of anthranilate synthase (OASA1D), 2-deoxyglucose (2-DOGR), benzyladenine-N-3-glucuronide, *E. coli* threonine deaminase, glutamate 1-semialdehyde aminotransferase (GSA-AT), D-amino acidoxidase (DAAO), salt-tolerance gene (rstB), ferredoxin-like protein (pflp), trehalose-6-P synthase gene (AtTPS1), lysine racemase (lyr), dihydrodipicolinate synthase (dapA), tryptophan synthase beta 1 (AtTSB 1), dehalogenase (dhlA), mannose-6-phosphate reductase gene (M6PR), hygromycin phosphotransferase (HPT), and D-serine ammonialyase (dsdA).

A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "label receptor" refers to incorporation of a heterologous polypeptide in the receptor. A label includes the incorporation of a radiolabeled amino acid or the covalent attachment of biotinyl moieties to a polypeptide that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as 35S or 131I) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

In certain embodiments, the disclosure relates to recombinant polypeptides comprising sequences disclosed herein or variants or fusions thereof wherein the amino terminal end or the carbon terminal end of the amino acid sequence are optionally attached to a heterologous amino acid sequence, label, or reporter molecule.

In certain embodiments, the disclosure relates to the recombinant vectors comprising a nucleic acid encoding a polypeptide disclosed herein or chimeric protein thereof.

In certain embodiments, the recombinant vector optionally comprises a mammalian, human, insect, viral, bacterial, bacterial plasmid, yeast associated origin of replication or gene such as a gene or retroviral gene or lentiviral LTR, TAR, RRE, PE, SLIP, CRS, and INS nucleotide segment or gene selected from tat, rev, nef, vif, vpr, vpu, and vpx or structural genes selected from gag, pol, and env.

In certain embodiments, the recombinant vector optionally comprises a gene vector element (nucleic acid) such as a selectable marker region, lac operon, a CMV promoter, a hybrid chicken B-actin/CMV enhancer (CAG) promoter, tac promoter, T7 RNA polymerase promoter, SP6 RNA polymerase promoter, SV40 promoter, internal ribosome entry site (IRES) sequence, cis-acting woodchuck post regulatory regulatory element (WPRE), scaffold-attachment region (SAR), inverted terminal repeats (ITR), FLAG tag coding region, c-myc tag coding region, metal affinity tag coding region, streptavidin binding peptide tag coding region, polyHis tag coding region, HA tag coding region, MBP tag coding region, GST tag coding region, polyadenylation coding region, SV40 polyadenylation signal, SV40 origin of replication, Col E1 origin of replication, fl origin, pBR322 origin, or pUC origin, TEV protease recognition site, loxP site, Cre recombinase coding region, or a multiple cloning site such as having 5, 6, or 7 or more restriction sites within a continuous segment of less than 50 or 60 nucleotides or having 3 or 4 or more restriction sites with a continuous segment of less than 20 or 30 nucleotides.

In certain embodiments, term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

In certain embodiments, sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example, the polypeptides GGGGGG (SEQ ID NO: 29) and GGGGT (SEQ ID NO: 30) have a sequence identity of 4 out of 5 or 80%. For example, the polypeptides GGGPPP (SEQ ID NO: 31) and GGGAPPP (SEQ ID NO: 32) have a sequence identity of 6 out of 7 or 85%. In certain embodiments, any recitation of sequence identity expressed herein may be substituted for sequence similarity.

Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic-A V I L; Charged positive: R K H; Charged negative—D E; Polar—S T N Q.

Overcoming TGF-β Mediated NK and CD8+ T-Cell Suppression by a IL-15 and TGF-β Receptor-Based Fusion Protein The use of cytokines as agents to augment immune responses against malignancies have been dealt setbacks due to immune selection of tumors, resulting in subpopulations that elaborate tumor-derived soluble factors, such as transforming growth factor-beta (TGF-β), which suppress immune effector functions. TGF-β is overexpressed by many solid tumors and inhibits the proliferation and anti-tumor functions of lymphomyeloid cells.

In order to maximize cytokine-based immunotherapy against tumors, a fusion protein was designed consisting of proinflammatory murine interleukin-15 (IL-15) linked to the sushi domain of the IL-15Rα chain (IL-15Rαsushi+IL-15) fused in frame to the C'-terminus of a dimeric murine TGF-β-receptor (type II, ectodomain-based ligand trap, termed FIST-15 (Fusion of Interleukin 15 with Sushi to TGF-β receptor). The rationale for the design of this protein is to prevent tumor derived TGF-β from suppressing the immune response via the TGF-β ligand trap moiety, while simultaneously providing a potent stimulus for the activation of antitumor responses by an IL-15R agonist (IL-15Rαsushi+IL-15).

FIST-15 can neutralize TGF-β induced SMAD signaling, and induce STAT3 and STATS phosphorylation by immunoblot, suggesting that both protein domains are biochemically active. Functionally, FIST-15 is able to induce primary NK– and CD8+ T-cell proliferation at rates greater than IL-15 alone and is capable of overcoming TGF-β mediated growth inhibition in these cells. Notably, rapid proliferation of the CD8+ central memory phenotype (CD62L+, CD44+) T-cells and upregulation of activation marker CD25 on these cells are seen with FIST-15 treatment. FIST-15 expanded NK– and CD8+ T-cells produce more IFN-γ and TNF-α compared to IL-15 expanded cells. While IL-15 expanded NK– and CD8+ T-cell production of these cytokines and anti-tumor effector molecules (e.g. Granzyme B) were significantly diminished by TGF-β co-treatment, FIST-15 expanded cells were relatively protected from the inhibitory effects of TGF-β.

Compositions and Conjugates

This disclosure relates to compositions and conjugates comprising an interleukin, e.g., IL-15 and a polypeptide that specifically binds TGF-beta. Typically the polypeptide that specifically binds TGF-beta is a type II TGF-beta receptor. In certain embodiments, the type II TGF-beta receptor is a human isoform, fragment or variant thereof. Uses for treating or preventing cancer and infectious diseases are contemplated.

In certain embodiments, IL-4, 7, 9, 15, and 21 are contemplated.

In certain embodiments, this disclosure relates to a composition comprising, jointly as conjugates or separately,
    (i) a first component selected from the group of
        (a) a polypeptide comprising an TGF-beta receptor polypeptide or a functionally equivalent variant thereof having at least 70% identity to said TGF-beta receptor polypeptide and
        (b) a polynucleotide encoding an TGF-beta receptor polypeptide or a functionally equivalent variant thereof having at least 70% identity to said TGF-beta receptor polypeptide and
    (ii) a second component selected from the group of
        (a) IL-15 or a functionally equivalent variant thereof having at least 70% identity to IL-15 and
        (b) a polynucleotide encoding IL-15 or a functionally equivalent variant thereof having at least 70% identity to IL-15 and
    (iii) a third component selected from the group of
        (c) the Sushi domain of the alpha chain of the IL-15 receptor or a functionally equivalent variant thereof having at least 70% identity to the Sushi domain of the alpha chain of the IL-15 receptor and
        (d) a polynucleotide encoding the Sushi domain of the alpha chain of the IL-15 receptor or a functionally equivalent variant thereof having at least 70% identity to the Sushi domain of the alpha chain of the IL-15 receptor.

The term "composition" as used in the present disclosure refers to a composition of material comprising the indicated components, e.g., the polypeptide TGF-beta receptor, IL-15 and the Sushi domain of the IL-15 receptor alpha chain as well as any other product resulting directly or indirectly from the combination of the different components in any quantities thereof. The expert in the art will appreciate that the composition may be formulated as a single formulation or may be presented as a formulation of each one of the components separately so that they can be combined for joint use in the form of a combined preparation. The composition may be a kit of parts wherein each component is separately formulated and packaged.

The term "protein", used herein indiscriminately with polypeptide, refers to a chain of amino acids of any length wherein the different amino acids are joined together by peptide bonds or disulphide bridges.

The term "polynucleotide", as used in the present disclosure, relates to a polymer formed by a variable number of monomers wherein the monomers are nucleotides, including ribonucleotides as well as deoxyribonucleotides. The polynucleotides include monomers modified by methylation as well as unmodified forms. The terms "polynucleotide" and "nucleic acid" are used indiscriminately in the present disclosure and include mRNA, cDNA and recombinant polynucleotides. As used in the present disclosure, polynucleotides are not limited to polynucleotides as they appear in nature, and also include polynucleotides where unnatural nucleotide analogues and inter-nucleotide bonds appear. Non-limitative examples of this type of unnatural structures include polynucleotides wherein the sugar is different from ribose, polynucleotides wherein the phosphodiester bonds 3'-5' and 2'-5' appear, polynucleotides wherein inverted bonds (3'-3' and 5'-5') appear and branched structures.

In certain embodiments, the first component of the disclosure is selected from the group of a TGF-beta receptor polypeptide or a functionally equivalent variant thereof and a nucleic acid encoding a TGF-beta receptor polypeptide or a functionally equivalent variant thereof.

The term "TGF-beta receptor", as used in the present disclosure relates to any member of the TGF-beta receptor family forming part of the high density lipoproteins (HDL) and that is capable of interacting specifically TGF-beta. Preferably, the TGF-beta receptor is a type II TGF-beta receptor such as a human isoform, fragment or variant thereof.

In certain embodiments, the type II TGF-beta receptor has greater than 50, 60, 70, 80, 90, 95, or 98% sequences identity or similarity to TIPPHVQKSVNNDMIVTDNN-GAVKFPQLCKFCDVRFSTCDNQKSCMSNC-SITSICEKPQE VCVAVWRKNDENITLETVCH-DPKLPYHDFILEDAASPKCIMKEKKKPGETFFM-CSCSSD ECNDNIIFSEEYNTSNPD (SEQ ID NO: 1).

In certain embodiments, the type II TGF-beta receptor has greater than 50, 60, 70, 80, 90, 95, or 98% sequences identity or similarity to MGRGLLRGLWPLHIVLWTRIASTIP-PHVQKSVNNDMIVTDNNGAVKFPQLCKFCDVRFS TCDNQKSCMSNCSITSICEKPQEVCVAVWRKNDEN-ITLETVCHDPKLPYHDFILEDAASP KCI-MKEKKKPGETFFMCSCSSDECNDNIIF-SEEYNTSNPDLLLVIFQVTGISLLPPLGVAI SVIIIFYCYRVNRQQKLSSTWETGKTRKLMEFSEH-CAIILEDDRSDISSTCANNINHNTE LLPIELD-TLVGKGRFAEVYKAKLKQNTSEQFETVAVKIFPY-EEYASWKTEKDIFSDINLK HENILQFLTAEERKTELGKQYWLITAFHAKGNLQEY-LTRHVISWEDLRKLGSSLARGIA HLHSDHTPCGRPKMPIVHRDLKSSNILVKNDLTC-
CLCDFGLSLRLDPTLSVDDLANSGQ VGTARYMAPE-
VLESRMNLENVESFKQTDVYSMALVLWEMTSRC-
NAVGEVKDYEPPFG
SKVREHPCVESMKDNVLRDRGR-
PEIPSFWLNHQGIQMVCETLTECWDHDPEARLTAQC
VAERFSELEHLDRLSGRSCSEEKIPEDGSLNTTK (SEQ
ID NO: 22) or fragment thereof.

In certain embodiments, the fragment is less than 550, 500, 450, 400, 350, 300, 350, 300, 250, 200, 150, or 100 amino acids.

Alternatively, the first component of the disclosure may be a nucleic acid showing a sequence identity of at least 70%, at least 75%, at least 80%, at least 85%, at least 90%, at least 91%, at least 92%, at least 93%, at least 94%, at least 95%, at least 96%, at least 97%, at least 98% or at least 99% with any of the abovementioned sequences wherein the percentage of identity is determined by using an algorithm of the GAP, BESTFIT or FASTA type whose computer implementation appears in the Wisconsin Genetics Software Package Release 7 (Wisconsin Genetics Software Package Release 7.0, Genetics Computer Group, 575 Science Dr., Madison, Wis.) and which uses the local algorithms of Smith and Waterman (Adv. Appl. Math., 1981, 2:482), of Needleman and Wunsch (J. Mol. Biol. 1970, 48: 443) or of Pearson and Lipman (Proc. Natl. Acad. Sci. (U.S.A.), 1988, 85:2444) using the default values for the different parameters.

Alternatively, the first component of the composition of the disclosure is a polynucleotide encoding TGF-beta receptor or a variant thereof capable of hybridizing specifically with any of the native sequences corresponding to TGF-beta receptor of different previously defined mammals. "Polynucleotides capable of hybridizing specifically with a target polynucleotide" is understood, in the context of the present disclosure, as meaning those polynucleotides capable of hybridizing in strict conditions, strict conditions understood as meaning the conditions that allow specific hybridization of two nucleic acids at temperatures of approximately 65° C. for example, in a solution of 6×SSC, 0.5% SDS, 5% Denhardt solution and unspecified denatured DNA at a concentration of 100 μg/ml any other solution with an equivalent ionic strength and following a stage of washing at 65° C. in the presence of a solution of, for example 0.2% SSC and 0.1% SDS and any other solution with an equivalent ionic strength. Nevertheless, the strict conditions may be adapted by the expert in the art according to the size of the sequence to be hybridized, according to the content in GC and according to other parameters. Suitable methods for selecting the appropriate hybridization conditions have been described by Sambrook et al., 2001 (Molecular Cloning: A Laboratory Manual, 3rd Edition, Laboratory Press, Cold Spring Harbor, N.Y.).

In certain embodiments, the second component is any interleukin such as a human IL-1, IL-2, IL-3, IL-4, IL-5, IL-6, IL-7, IL-8, IL-9, IL-10, IL-11, IL-12, IL-13, IL-15, IL-17, or combinations thereof.

In certain embodiments, the compositions or conjugates comprise IL-15, e.g., a human isoform, fragment or variant thereof.

In certain embodiments, IL-15 has greater than 50, 60, 70, 80, 90, 95, or 98% sequences identity or similarity to NWVNVISDLKKIEDLIQSMHIDATLYTESDVHP-
SCKVTAMKCFLLELQVISLESGDASIH DTVEN-
LIILANNSLSSNGNVTESGCKECEELEEKNIKE-
FLQSFVHIVQMFINTS (SEQ ID NO: 2).

In certain embodiments, IL-15 has greater than 50, 60, 70, 80, 90, 95, or 98% sequences identity or similarity to MRISKPHLRSISIQCYLCLLLNSHFLTEAGIHV-
FILGCFSAGLPKTEANWVNVISDLKKIED LIQSMHI-
DATLYTESDVHPSCKVTAMKCFLLELQVISLESG-
DASIHDTVENLIILANNSLSS
NGNVTESGCKECEELEEKNIKEFLQSFVHIVQM-
FINTS (SEQ ID NO: 23). In certain embodiments, the fragment is less than 150, 130, 110, 90, 70, 50, or 30 amino acids.

In certain embodiments, the compositions or conjugates further comprises a sushi domain of the IL-15 receptor alpha chain. In certain embodiments, the sushi domain of the IL-15 receptor alpha chain greater than 50, 60, 70, 80, 90, 95, or 98% sequences identity or similarity to CPPPMSVE-
HADIWVKSYSLYSRERYICNSGFKRK-
AGTSSLTECVLNKATNVAHWTTPSL KC (SEQ ID NO:3).

In certain embodiments, the second component of the disclosure is selected from the group of IL-15 or a functionally equivalent variant thereof and of a nucleic acid encoding IL-15 or a functionally equivalent variant thereof.

The term "IL-15", refers to a cytokine whose isolation, cloning and sequence is described in Grabstein et al. (U.S. Pat. No. 5,747,024 and Grabstein et al., 1994, Science 246: 965-968). The term IL-15 includes any polypeptide form with the amino acid sequence of a natural IL-15. Examples of IL-15 that may be used forming part of the compositions and fusion proteins of the present disclosure include, IL-15 of rodents (mouse, rat, hamster), human, primate, canine, feline, porcine, equine, bovine, ovine, and similar. IL-15 polypeptides of mammals that can form part of the compositions and fusion proteins of the disclosure include, without limitation, IL-15 of human origin and whose amino acid sequence is the one shown in P40933 (SEQ ID NO: 2); mouse IL-15 whose amino acid sequence is shown in P48346, rat IL-15 whose amino acid sequence is shown in P97604, cat IL-15 whose amino acid sequence is shown in 097687 and bovine IL-15 whose amino acid sequence is the one shown in Q28028.

"Functionally equivalent variant of IL-15" is understood as meaning all those polypeptides resulting from the insertion, substitution or deletion of one or more amino acids from any of the abovementioned sequences of IL-15 and that maintain substantially intact at least one of the functions of IL-15, wherein said function is selected from:

The capacity to promote the proliferation of CD8+ T cells determined, for example, by the method described by Montes, et al, (Clin. Exp. Immunol., 2005, 142:292-302) based on the incubation of a population of peripheral blood mononuclear cells with an antigen peptide in the presence of the variant of IL-15 followed by the determination of the percentage of cells that can be labelled with specific antibodies against CD8, The capacity to promote the activation of NK cells after being presented in trans by the dendritic cells. This capacity may be determined by measuring the incorporation of tritiated thymidine on the part of the CD56+NK cells in the presence of IL-15 or by measuring the NK cell secretion of the GM-CSF cytokine. Methods for determining both IL-15 functionalities have been described by Carson, W. et al. (J. Exp. med., 1994, 180:1395-1403), macrophages and neutrophils.

The capacity of IL-15 to inhibit Fas-mediated apoptosis in B-cell precursors, as described by Demirci et al. (Cell Mol Immunol. 2004, 1:123-8.), which can be determined using standard techniques for determining apoptosis such as TUNEL or the determination of DNA fragmentation by gel electrophoresis and ethidium bromide staining.

Variants of IL-15 contemplated in the context of the present disclosure include polypeptides showing at least 70%, 72%, 74%, 76%, 78%, 80%, 90%, or 95% of similarity or identity with the IL-15 polypeptides of the mammals mentioned above. The degree of identity between two polypeptides is determined using computer-implemented algorithms and methods that are extensively known to experts in the art. The identity between two amino acid sequences is preferably determined using the BLASTP algorithm (BLAST Manual, Altschul, S. et al., NCBI NLM NIH Bethesda, Md. 20894, Altschul, S., et al., J., 1990, Mol. Biol. 215:403-410).

The second component of the disclosure can be a nucleic acid encoding at least one of the native IL-15 and variants of IL-15 mentioned above. The nucleic acids encoding mammal IL-15 can be recovered from nucleic acid repositories and include, without limitation, polynucleotides whose sequences are defined by accession numbers U14407.

Said polynucleotides include those that show a sequence identity of at least 70%, at least 75%, at least 80%, at least 85%, at least 90%, at least 91%, at least 92%, at least 93%, at least 94%, at least 95%, at least 96%, at least 97%, at least 98% or at least 99% identity with any of the aforesaid sequences wherein the percentage of identity is determined by using one of the algorithms mentioned above.

Alternatively, the polynucleotides forming the second component of the disclosure are polynucleotides capable of hybridizing specifically with the previously defined polynucleotides. Methods for determining a polynucleotide's capacity to hybridize specifically with a target sequence have been described in detail in the context of the first component of the disclosure.

The expert in the art will appreciate that the nucleic acid forming the second component of the disclosure can be found operatively bound to a signal sequence allowing secretion into the medium of the IL-15 or functionally equivalent variant. Suitable signal sequences for use in the present disclosure include those mentioned previously in the context of the first component of the disclosure. In certain embodiments, the signal sequence forming part of the second component of the composition of the disclosure is the signal sequence of IL-15 itself as previously defined or the signal sequence of one of the immunoglobulins, in particular IgκK or IgV$_\chi$. Typically, the signal peptide of IL-15 is not utilized in FIST-15 conjugate to direct the secretion of the protein. In certain embodiments, a VEGF signal peptide (MNFLLSWVHWSLALLLYLHHAKWSQA) (SEQ ID NO: 28) is used for protein secretion. Experimental data indicates that embedding the IL-15 signal peptide N-terminal to mature IL-15 reduces the signaling capacity and bioactivity of the IL-15 moiety.

In certain embodiments, a component of the disclosure is selected from the group of the sushi domain of the IL-15 receptor alpha chain or a functionally equivalent variant thereof.

The expression "sushi domain of the IL-15 receptor alpha chain" (hereinafter IL-15Rα-sushi), as used in the present disclosure, refers to an amino acid sequence that appears in the extracellular region of the IL-15 receptor alpha chain and that corresponds to the sequence beginning with the first cysteine to appear in the first exon of the gene of the IL-15 receptor alpha chain and ending with the cysteine encoded by exon 4 of the gene of the IL-15 receptor alpha chain. Alternatively, the sushi domain is defined as the sequence starting in the first cysteine residue of the IL-15 receptor alpha chain after the signal sequence and ending with the fourth cysteine residue after the signal sequence in the aforesaid sequence. Suitable sushi domains for use in the present disclosure include the sushi domain from the human origin IL-15 receptor alpha chain, corresponding to the sequence with UniProt accession number NP-002180 and whose Sushi domain corresponds to the sequence (SEQ ID NO: 3)
CPPPMSVEHADIWVKSYSLYSRERYICNSGFKRKAGTSSLTECVLNKATN
VAHWTTPSLKC and the sushi domain from the mouse IL-15 receptor alpha chain corresponding to the sequence with Swiss-Prot accession number Q60819 and whose Sushi domain corresponds to the sequence (SEQ ID NO: 4)
CPPPVSIEHADIRVKNYSVNSRERYVCNSGFKRKAGTSTLIECVINKNTN
VAHWTTPSLKC.

"Functionally equivalent variant of the sushi domain of the IL-15 receptor alpha chain" is understood as meaning all those polypeptides resulting from the insertion, substitution or deletion of one or more amino acids of the sequence of any of the sequences of human origin or murine sushi domains mentioned previously and that maintain substantially intact their capacity to bind to IL-15 and increase the proliferative effect of IL-15 in cells expressing the low affinity IL-15 receptor (for example, cells from Mo-7e or 32Dβ lines) as described by Mortier et al. (J. Biol. Chem., 2006, 281:1612-1619).

Variants of IL-15Rα-sushi contemplated in the context of the present disclosure include polypeptides showing at least 70%, 72%, 74%, 76%, 78%, 80%, 90%, or 95% similarity or identity with the polypeptides mentioned above. The degree of identity between two polypeptides is determined using computer-implemented algorithms and methods extensively known to experts in the art. The identity between two amino acid sequences is determined preferably by using the BLASTP algorithm (BLAST Manual, Altschul, S. et al., NCBI NLM NIH Bethesda, Md. 20894, Altschul, S., et al., J., 1990, Mol. Biol. 215:403-410).

The third component of the disclosure may be a nucleic acid encoding at least one sushi domain of the IL-15 receptor alpha chain, native and variants thereof as mentioned previously. The nucleic acids encoding mammal IL-15Rα-sushi can be recovered from the sequences of the corresponding alpha chains found in the nucleic acid repositories and include, without limitation, the sequences encoding IL-15Rα-sushi of the human IL-15 receptor alpha chain.

The compositions and conjugates of the disclosure may be formed by polypeptides or polynucleotides from different species. Nonetheless, in a preferred embodiment the three components originate from the same animal species. In a preferred embodiment, the three components are of human origin. In another preferred embodiment, the three components are of murine origin.

In certain embodiments, compositions or conjugates disclosed herein may further comprise an ApoA polypeptide. "ApoA polypeptide" refers to any member of the Apo A family forming part of the high density lipoproteins (HDL) and that is capable of interacting specifically with receptors on the surface of liver cells thereby guaranteeing its capacity to transport the molecules of interest to this organ joined to the aforesaid Apo A protein. Preferably, the Apo A molecules that can be used in the present invention are selected from the group of ApoA-I, ApoA-II, ApoA-III, ApoA-IV and ApoA-V or of functionally equivalent variants thereof.

In a preferred embodiment, the Apo A protein that is used in the present disclosure is the protein ApoA-I. ApoA-I is understood, in the context of the present disclosure, as the mature form of the pre-proApoA-I protein which forms part of high density lipoproteins (HDL). ApoA-I is synthesised as a precursor (pre-proApoA-I) containing a secretion signal sequence that is eliminated to make way for the precursor. The signal sequence consists of 18 amino acids, the pro-peptide of 6 and the mature form of the protein of 243 amino acids. Preferably the mature protein form is used lacking the peptide signal and processed. In a preferred embodiment, the ApoA-I protein is of human origin and its amino acid sequence is UniProt accession number P02647.

In certain embodiments, the disclosure contemplates that the first and second components of the composition are polypeptides, said single molecule is a fusion protein comprising (i) a TGF-beta receptor polypeptide or functionally equivalent variant thereof and (ii) IL-15 or a functionally equivalent variant thereof.

The term "fusion protein", as used in the present disclosure, refers to polypeptides comprising two or more regions from different or heterologous proteins.

Alternatively, in the case of both the first and second components of the composition being polynucleotides, said single molecule is a polynucleotide encoding a fusion protein comprising (i) a polypeptide comprising a TGF-beta receptor polypeptide or a functionally equivalent variant thereof and (ii) IL-15 or a functionally equivalent variant thereof.

In this case, when the first and second components are of a peptidic nature, the disclosure contemplates compositions wherein the first component is in the N-terminal position in relation to the second component, and compositions wherein the first component is in the C-terminal position in relation to the second component.

In the case of the first and second components being of a polynucleotidic nature, the disclosure contemplates compositions wherein the first component is in position 5' in relation to the second component, and compositions wherein the first component is in position 3' in relation to the second component.

In both cases, it is possible for the first and second component to be associated directly, in other words, the C-terminal end of the first component is associated to the N-terminal end of the second component, or the C-terminal end of the second component is associated to the N-terminal end of the first component, or the 3' end of the first component is associated to the 5' end of the second component and compositions wherein the 3' end of the second component is associated to the 5' end of the first component.

Alternatively, in another aspect, the disclosure contemplates compositions wherein the fusion of the first and second component is carried out through a peptide linker (in the case of the first and second component being of a polypeptidic nature) or through a sequence encoding a peptide linker (in the case of the first and second component being of a polynucleotidic nature).

The term "peptide linker", "linker", "connector", "spacer" or its grammatical equivalents, as used in the present disclosure, refers to a molecule that connects two molecules and that frequently allows connected molecules to acquire a functional configuration. The linker peptide preferably comprises at least two amino acids, at least three amino acids, at least five amino acids, at least ten amino acids, at least 15 amino acids, at least 20 amino acids, at least 30 amino acids, at least 40 amino acids, at least 50 amino acids, at least 60 amino acids, at least 70 amino acids, at least 80 amino acids, at least 90 amino acids or approximately 100 amino acids.

Suitable linkers for use in the present disclosure include linkers comprising 2 amino acids or more selected from the group consisting of glycine, serine, alanine and threonine such as, without limitation the linkers of sequence SGGTSGSTSGTGST (SEQ ID NO: 5), AGSSTGSSTGPG-STT (SEQ ID NO: 6), GGSGGAP (SEQ ID NO: 7) and GGGVEGGG (SEQ ID NO: 8) described by Muller, K. M. et al. (Methods. Enzimology, 2000, 328: 261-281).

Linkers based on residues 53-56 of tetranectin, which form a sheet in tetranectin, and residues 57-59 which form a turn in tetranectin (Nielsen, B. B. et al., FEBS Lett. 412: 388-396, 1997) such as the linker of sequence GTKVHMK (SEQ ID NO:9), Linkers based on a subsequence of the linker sheet 3 of human fibronectin, corresponding to amino acids 1992-2102 such as the linker PGTSGQQPSVGQQ (SEQ ID NO: 10) corresponding to amino acids number 2037-2049, and within that subsequence fragment GTSGQ (SEQ ID NO: 11) corresponding to the residues of amino acids 2038-2042 is more preferable.

Linkers based on the sequence of 10 residues of amino acids of the upper hinge region of murine IgG3 such as the linker of sequence PKPSTPPGSS (SEQ ID NO: 12) which has been used for the production of dimeric antibodies by means of a coiled helix (Pack P. and Pluckthun, A., 1992, Biochemistry 31:1579-1584), linker peptide of sequence GGSSGG (SEQ ID NO: 13), and linker peptide of sequence GGSGGGGSGGGSGGGGSLQ (SEQ ID NO: 14).

Alternatively, the two components of the conjugates of the disclosure can be connected by a peptide whose sequence contains a cleavage target for a protease, thereby allowing separation of TGF-β receptor from component (ii). Suitable protease cleavage sites for incorporation into the polypeptides of the disclosure include enterokinase (cleavage site DDDDK SEQ ID NO: 15), Xa factor (cleavage site IEDGR, SEQ ID NO: 16), thrombin (cleavage site LVPRGS, SEQ ID NO: 17), TEV protease (cleavage site ENLYFQG, SEQ ID NO:18), PreScission protease (cleavage site LEVLFQGP, SEQ ID NO:19), inteins and similar. In certain embodiments, the cleavage site is that of a protease expressed in tumoral tissues, inflamed tissues or in the liver in such a way that separation of TGF-β receptor and component (ii) takes place once the conjugate has reached the liver. In certain embodiments, the linker contains a matrix metalloproteinase 9 recognition site (cleavage site LFPTS, SEQ ID NO: 20).

Although the disclosure has been exemplified with compositions wherein both the component resulting from the fusion of the first and second component (the fusion protein of TGF-β receptor with IL-15) and the third component (the Sushi domain of the IL-15 receptor α chain) are used in the form of a nucleic acid, the disclosure is not limited to compositions wherein both components are nucleic acids and rather contemplates, as alternatives, compositions wherein the first and/or second component are polypeptides.

In certain embodiments, the disclosure relates to a polypeptide comprising a fusion protein formed by TGF-β receptor and IL-15 and a polypeptide comprising the sushi domain of the IL-15 receptor α chain.

In certain embodiments, the disclosure relates to a polypeptide comprising a fusion protein formed by TGF-β receptor and IL-15 and a polynucleotide encoding a polypeptide comprising the sushi domain of the IL-15 receptor α chain.

In certain embodiments, the disclosure relates to a polynucleotide encoding a polypeptide comprising a fusion protein formed by TGF-β receptor and IL-15 and a poly-peptide comprising the sushi domain of the IL-15 receptor α chain.

In certain embodiments, the disclosure relates to a poly-nucleotide encoding a polypeptide comprising a fusion protein formed by TGF-β receptor and IL-15 and a poly-nucleotide encoding a polypeptide comprising the sushi domain of the IL-15 receptor α chain.

The ratio between the components forming part of the compositions of the disclosure will depend on the inductor agent of the first and second component used in each particular case, as well as the required use. Thus, the disclosure contemplates compositions wherein the ratio between the amounts of the two components can range between 50:1 and 1:50, in particular between 20:1 and 1:20, between 1:10 and 10:1, or between 5:1 and 1:5.

In the case of compositions wherein the first and second component form a single molecule, each one of the com-ponents may come from a different species, although it is preferred for the components forming part of a single molecule to come from the same species. Thus, in a pre-ferred embodiment, TGF-β receptor or the functionally equivalent variant thereof is of human origin and IL-15 or the functionally equivalent variant thereof is of human origin. In another preferred embodiment, TGF-β receptor or the functionally equivalent variant thereof is of murine origin and IL-15 or the functionally equivalent variant thereof is of murine origin.

In certain embodiments, the single molecule forming the first component of the composition is formed by the human origin TGF-β receptor polypeptide and human origin IL-15, separated by a linker presenting the GAP sequence.

The polypeptide comprising the Sushi domain of the IL-15 receptor alpha chain or the functionally equivalent variant thereof may be of human origin or murine origin. Nonetheless, if the components forming the single molecule are both of human origin, it is preferable for the Sushi domain of the IL-15 receptor alpha chain or functionally equivalent variant thereof to also be of human origin. Alternatively, if the components forming the single mol-ecule are both of murine origin, it is preferred for the Sushi domain of the IL-15 receptor alpha chain or functionally equivalent variant thereof to also be of murine origin.

In certain embodiments, the disclosure relates to a fusion protein comprising structure of the protein in A-B-C orien-tation. In certain embodiments, FIST-15 is the TGF-beta receptor followed by the sushi domain followed by IL-15:

(i) a region A formed by an TGF-β receptor polypeptide or repeating TGF-β receptor polypeptide or a function-ally equivalent variant thereof having at least 70% identity to said TGF-β receptor polypeptide, (ii) a region B formed by the Sushi domain of the IL-15 receptor alpha chain or a functionally equivalent vari-ant thereof having at least 70% identity to the Sushi domain of the IL-15 receptor alpha chain, and (iii) a region C formed by IL-15 or a functionally equiva-lent variant thereof having at least 70% identity to IL-15 and In certain embodiments, region A of the fusion protein essentially coincides with the first component of the com-positions of the disclosure.

In certain embodiments, region B of the fusion protein essentially coincides with the second component of the compositions of the disclosure.

In certain embodiments, region C of the fusion protein essentially coincides with the third component of the com-positions of the disclosure.

In certain embodiments, the fusion protein of the disclo-sure may present different arrangements of regions A, B and C. Thus, the disclosure contemplates:

a fusion protein wherein region A is in the N-terminal position, region B is in the central position and region C is in the C-terminal position, a fusion protein wherein region A is in the N-terminal position, region C in the central position and region B in the C-terminal position, a fusion protein wherein region B is in the N-terminal position, region A is in the central position and region C is in the C-terminal position, a fusion protein wherein region B is in the N-terminal position, region C is in the central position and region A is in the C-terminal position, a fusion protein wherein region C is in the N-terminal position, region A is in the central position and region B is in the C-terminal position and a fusion protein wherein region C is in the N-terminal position, region B is in the central position and region A is in the C-terminal position.

In certain embodiments, regions A, B and/or C can be directly associated, in other words, wherein the C-terminal amino acid of a region is joined by a peptide bond to the N-terminal amino acid of another region. Alternatively, the different regions are joined together by a peptide linker. Suitable linkers for the fusion protein of the disclosure are essentially the same as used in the composition of the disclosure and have been described in detail above. The expert in the art will appreciate that the fusion protein may contain one or two peptide linkers depending on whether only two of the three regions are associated together by a linker or whether the three regions are associated by linkers.

In certain embodiments, the fusion protein presents a B-C-A-type arrangement, in other words, comprises, in the direction N-to C terminal, the Sushi domain of IL-15Rα (region B), IL-15 (region C) and TGF-β receptor (region A). In an even more preferred embodiment, regions C and B are separated by a linker of type GGSGGGGSGGGSGGGGSLQ (SEQ ID NO: 14). In another embodiment, regions B and A are separated by a GAP-type linker. In an even more preferred embodiment, regions C and B are separated by a linker of type GGSGGGGSGGGSGGGGSLQ (SEQ ID NO: 14) and regions B and A are separated by a GAP-type linker.

Although the fusion proteins of the disclosure are exem-plified with fusion proteins wherein regions A, B and C are of murine origin, the expert in the art will appreciate that the disclosure contemplates fusion proteins wherein each one of the regions A, B and C may be of different origin, from among the different variants of the regions mentioned above.

Thus, in a preferred embodiment, the fusion protein comprises a region A of human origin or murine origin, a region B of human origin or murine origin, a region C of human origin or murine origin. In an even more preferred embodiment, the three regions come from the same organ-ism. Thus, in an even more preferred embodiment, regions A, B and C are of murine origin. In another preferred embodiment, regions A, B and C are of human origin.

In a preferred embodiment, the fusion protein presents an arrangement of the C-B-A type wherein the three compo-nents are of human origin and wherein both regions C and B as well as regions B and A are connected by peptide linkers. In a preferred embodiment, the fusion protein com-prises, in the direction N-to C-terminal, the sushi domain of human IL-15Rα (region C), human IL-15 (region B) and human TGF-beta receptor (region A). In an even more preferred embodiment, regions C and B are separated by a linker of type GGSGGGGSGGGSGGGGSLQ (SEQ ID NO: 14). In another embodiment, regions B and A are separated by a GAP-type linker. In an even more preferred embodiment, regions C and B are separated by a linker of type GGSGGGGSGGGSGGGGSLQ (SEQ ID NO:14) and regions B and A are separated by a GAP-type linker.

In a preferred embodiment, the fusion protein comprises the sequence defined by SEQ ID NO: 21.

In another preferred embodiment, the fusion protein comprises, in the direction N-to C terminal, the sushi domain of murine IL-15Rα (region C), murine IL-15 (region B) and murine TGF-beta receptor (region A). In an even more preferred embodiment, regions C and B are separated by a linker of type GGSGGGGSGGGSGGGGSLQ (SEQ ID NO: 14). In another embodiment, regions B and A are separated by a GAP-type linker. In an even more preferred embodiment, regions C and B are separated by a linker of type GGSGGGGSGGGSGGGGSLQ (SEQ ID NO: 14) and regions B and A are separated by a GAP-type linker.

Polynucleotides, Gene Constructs, Vectors and Host Cells

In certain embodiments, the disclosure contemplates a polynucleotide encoding the fusion protein of the disclosure. Given that the fusion protein of the disclosure performs its function from the extracellular medium, it is convenient for the polynucleotide to encode the fusion protein of the disclosure with a signal sequence that allows the fusion protein access to the secretory pathway and the fusion protein's secretion into the medium. Suitable signal sequences for use together with the fusion protein include both the signal sequence of any of the fusion protein components (the signal sequence of TGF-beta receptor, signal sequence of IL-15 or signal sequence of the IL-15 receptor a chain) or any signal sequences mentioned above in the context of the first component of the composition of the disclosure, in other words, suitable signal sequences of tissue plasminogen activator (tPA), of the growth hormone, of GM-CSF and of immunoglobulins, and, in particular the signal sequences of Igκ or of IgV$_χ$.

In certain embodiments, the polynucleotide of the disclosure comprises the sequence encoding a fusion protein or conjugate comprising the human origin TGF-beta receptor followed by a human origin Sushi domain, human origin IL-15 and wherein the Sushi domain and IL-15 are separated by a linker of sequence, wherein IL-15 and TGF-beta receptor are separated by a linker of sequence GAP and wherein the fusion is preceded by the signal sequence of the human origin IL-15 receptor alpha chain.

In certain embodiments, the polynucleotide of the disclosure comprises the sequence encoding a fusion protein or conjugate comprising the human origin Sushi domain, human origin IL-15 and human origin TGF-beta receptor, wherein the Sushi domain and IL-15 are separated by a linker of sequence, wherein IL-15 and TGF-beta receptor are separated by a linker of sequence GAP and wherein the fusion is preceded by the signal sequence of the human origin IL-15 receptor alpha chain.

The polynucleotide that encodes the fusion protein of the disclosure can be operatively associated to a regulatory region of expression thereby giving rise to a gene construct. Therefore, in another aspect, the disclosure relates to a gene construct comprising a polynucleotide of the disclosure. Preferably, the construct comprises the polynucleotide of the disclosure placed under the operational control of sequences that regulate the expression of the polynucleotide of the disclosure. The expert in the art will appreciate that the polynucleotides of the disclosure must access the nucleus of a target tissue and therein be transcribed and translated to give rise to the biologically active fusion protein.

In principle, any promoter can be used for the gene constructs of the present disclosure on condition that said promoter is compatible with the cells in which the polynucleotide is to be expressed. Thus, suitable promoters for carrying out the present disclosure include, without necessarily limitation, constitutive promoters such as those derived from the genomes of eukaryote viruses such as the polyomavirus, adenovirus, SV40, CMV, bird sarcoma virus, hepatitis B virus, the metallothionein gene promoter, the thymidine kinase gene promoter of the herpes simplex virus, LTR regions of retroviruses, the immunoglobulin gene promoter, the actin gene promoter, the EF-1alpha gene promoter as well as inducible promoters wherein the expression of the protein depends on the addition of a molecule or exogenous signal, such as the tetracycline system, the NFκB/UV light system, the Cre/Lox system and the heat shock gene promoter, regulable promoters of RNA polymerase II described in WO/2006/135436 as well as specific tissue promoters.

The polynucleotides of the disclosure or gene constructs comprising them may form part of a vector. Thus, in another aspect, the disclosure relates to a vector which comprises a polynucleotide or a gene construct of the disclosure. The expert in the art will appreciate that there is no limitation in terms of the type of vector that can be used since said vector may be a cloning vector suitable for propagation and for obtaining the suitable polynucleotides or gene constructs, or expression vectors in different heterologous organisms suitable for purifying the conjugates. Thus, suitable vectors in accordance with the present disclosure include expression vectors in prokaryotes such as pUC18, pUC19, Bluescript and its derivatives, mp18, mp19, pBR322, pMB9, ColEI, pCRI, RP4, phages and "shuttle" vectors such as pSA3 and pAT28, expression vectors in yeasts such as 2-micra plasmid-type vectors, integration plasmids, YEP vectors, centromeric plasmids and similar, expression vectors in insect cells such as the pAC-series and pVL-series vectors, expression vectors in plants such as vectors of series pIBI, pEarleyGate, pAVA, pCAMBIA, pGSA, pGWB, pMDC, pMY, pORE and similar and expression vectors in superior eukaryotic cells well based in viral vectors (adenovirus, viruses associated to adenovirus as well as retrovirus and lentivirus) in addition to non-viral vectors such as pSilencer 4.1-CMV (Ambion), pcDNA3, pcDNA3.1/hyg pHCMV/Zeo, pCR3.1, pEFI/His, pIND/GS, pRc/HCMV2, pSV40/Zeo2, pTRACER-HCMV, pUB6/V5-His, pVAXI, pZeoSV2, pCI, pSVL and pKSV-10, pBPV-1, pML2d and pTDTI.

The vector of the disclosure can be used to transform, transfect or infect cells prone to transformation, transfection or infection by said vector. Said cells can be prokaryotic or eukaryotic. By way of an example, the vector wherein said DNA sequence is introduced may be a plasmid or a vector that, when introduced in a host cell, integrates in said cell's genome and replicates together with the chromosome (or chromosomes) into which it has been integrated. Said vector may be obtained by conventional methods known to technicians in the art (Sambrook et al., 2001, quoted supra).

In certain embodiments, the disclosure relates to a cell comprising a polynucleotide, a gene construct or a vector of the disclosure, wherefore it has been possible to transform, transfect or infect said cell with a construct or vector provided by this disclosure. Transformed, transfected or infected cells can be obtained by conventional methods known to experts in the art (Sambrook et al., 2001, quoted supra). In a particular embodiment, said host cell is an animal cell transfected or infected with an appropriate vector.

Suitable host cells for the expression of the conjugates of the disclosure include, without limitation, the cells of mammals, plants, insects, fungi and bacteria. Bacterial cells include, without limitation, the cells of Gram-positive bacteria such as species of the genus *Bacillus, Streptomyces* and *Staphylococcus* and cells of Gram-negative bacteria such as cells of the genus *Escherichia* and *Pseudomonas*. Fungal cells include, preferably, yeast cells such as *Saccharomyces, Pichia pastoris* and *Hansenula polymorpha*. Insect cells include, without limitation, cells of *Drosophila* and Sf9 cells. Plant cells include, among others, cells from crop plants such as cereals, medicinal or ornamental plants or bulbs. Suitable mammal cells for the present disclosure include epithelial cell lines (porcine, etc.), osteosarcoma cell lines (human, etc.), neuroblastoma cell lines (human, etc.), epithelial carcinomas (human, etc.), glial cells (murine, etc.), liver cell lines (monkey, etc.). CHO cells (Chinese Hamster Ovary), COS cells, BHK cells, cells HeLa, 911, AT1080, A549, 293 or PER.C6, human ECCs NTERA-2 cells, D3 cells of the line of mESCs, human embryonic stem cells such as HS293 and BGV01, SHEF1, SHEF2 and HS181, cells NIH3T3, 293T, REH and MCF-7 and hMSCs cells.

In Vitro Methods

The capacity of IL-15 to promote the proliferation of antigen-sensitized T lymphocytes has been described. Thus, it has been demonstrated that contacting a population of isolated lymphocytes previously exposed to a determined antigen with IL-15 results in an increase in lymphocyte proliferation. This expanded lymphocyte population can be used in adoptive immunotherapy whereby it is subsequently re-administered to the patient from which said initial population has been obtained. Therefore, in another aspect, the disclosure relates to an in vitro method for promoting the expansion of antigen-specific T lymphocytes comprising contacting a population of lymphocytes previously exposed to said antigen with a composition of the disclosure, a fusion protein of the disclosure, a polynucleotide of the disclosure, a vector of the disclosure, a gene construct of the disclosure or a host cell of the disclosure.

The term "expansion" is used in the present disclosure indiscriminately with proliferation and must be understood as cell division or cell growth. The expansion may be determined using extensively known methods, such as, for example, the methods described in Transplantation (1999) 67: 605-613.

The expression "antigen-specific T lymphocytes", as used in the present disclosure, refers to a lymphocyte population capable of recognising a specific antigen. Typically, lymphocytes are isolated from a patient who has been exposed to said antigen. Alternatively, the antigen may be placed in contact with the lymphocyte population in an artificial antigen-presenting system as described in U.S. Pat. No. 6,828,150 or 6,787,154.

The term "antigen", as used in the present disclosure, refers to any substance capable of triggering an immune response in a subject who is intolerant to said antigen. The antigen may come from the subject himself, in which case it is an autoantigen, or may be an alloantigen, in other words, an antigen derived from an individual of the same species. Alternatively, the antigen may be a xenoantigen, in other words, an antigen derived from an individual of a different species.

The lymphocytes that can be used in the method of the present disclosure include, without limitation, cytotoxic T lymphocytes (CTL), T helper cells, lymphokine-activated cells, tumor-infiltrating lymphocytes (TILS), NK cells, naive cells, memory cells, gamma delta T cells, NKT cells as well as cell populations comprising variable quantities of one or more of the aforesaid cells. In a preferred embodiment, the lymphocytes are CTL. Suitable methods for obtaining CTLs for subsequent expansion in vitro using the method of the disclosure are extensively known to an expert in the art and include, without limitation, isolation from peripheral blood, from umbilical cord blood, from tissues containing lymphocytes. In a preferred embodiment, the lymphocytes are isolated through drainage from the lymph nodes of patients suffering from a particular disease.

Once the lymphocytes have been isolated, they are placed in contact with a composition of the disclosure, a fusion protein of the disclosure, a polynucleotide of the disclosure, a vector of the disclosure, a gene construct of the disclosure or a host cell of the disclosure in suitable conditions for lymphocyte expansion to take place. The general conditions for antigen-specific CTL expansion can be established according to well-known methods [for example, Carter J. et al., Immunology, 57 (1), 123-129, (1996)] and may be routinely optimised by an expert in the art. Typically, contacting the lymphocytes with the composition, fusion protein, polynucleotide, vector, gene construct or host cell of the disclosure is carried out by means of culturing the lymphocytes in a suitable medium for said cells. The cells may be cultured under conventional conditions in a suitable medium for growing lymphocytes which include a Minimum Essential Medium or RPMI 1640 Medium. With a view to promoting cell growth, necessary proliferation and viability factors may be added including serum, for example, foetal calf serum or human serum and antibiotics, for example, penicillin, streptomycin. The lymphocytes are kept in the necessary conditions for supporting growth, for example, at a suitable temperature of about 37° C. and atmosphere, for example, air plus 5% CO2.

In certain embodiments, the lymphocytes can be treated prior to their stimulation using the compounds of the disclosure to promote their activation in vitro, by contacting the lymphocytes with the antigen against which they are specific. This is particularly necessary in the case of patients with tumors producing immunosuppressant substances. To achieve this, it is necessary to stimulate the lymphocyte's culture with the appropriate antigen. Typically, the antigen is presented to the T cell in such a way that the signal is triggered in the T cell through the TCR/CD3 complex. Preferably, the antigen can be presented to the T cell by means of an antigen-presenting cell.

The expression "antigen-presenting cell", as used in the present disclosure, refers to a cell that contributes to generating the immune response by means of presenting an antigen to the T lymphocytes. Antigen-presenting cells include dendritic cells, mononuclear phagocytes, B lymphocytes or Langerhans cells. Antigen-presenting cells may be isolated, for example, from the bone marrow, blood, thymus, epidermis, liver or foetal liver.

In the case of the antigen being a tumoral antigen, it is possible to use an extract of the autologous tumor and/or a recombinant tumor antigen. In the case of an antigen from a pathogen, the lymphocyte activation prior to expansion can be carried out using a pathogen-infected cell, for example a virus presenting antigens of the pathogen.

In certain embodiments, it is preferable for the treatment of the cells with the compositions, fusion proteins of the disclosure to be carried out in the presence of an anti-CD3 antibody and, preferably, with a human monoclonal anti- CD3 antibody, and more preferably with OKT3. The concentration of anti-CD3 antibodies during the expansion process is not especially limited and is, for example, 0.001 to 100 mg/mL, and more preferably 0.01 to 100 mg/mL. Additionally or alternatively, the cells may be co-cultured with an anti-CD28 antibody, and more preferably with a human monoclonal anti-CD28 antibody. Additionally or alternatively, the cells can be co-cultured with a lymphocyte-stimulating factor, such as a lectin. Also, one or more of these components can be immobilized to a solid phase.

In certain embodiments, the cells can be co-cultured with feeder cells according to the circumstances. In principle, there is no limitation in terms of the type of feeder cells that can be used on condition that said feeder cells cooperate with the protein or composition of the disclosure or with the agents mentioned in the previous paragraph in the capacity to promote CTL-proliferation. Preferably, suitable feeder cells include, without limitation peripheral blood mononuclear cells (PBMCs) and autologous or non-autologous EBV-B cells. Normally, the feeder cells are treated once used to eliminate their proliferation capacity, preferably through treatment with X-rays or cytotoxic agents such as mitomycin.

The cytotoxic activity of the lymphocyte population obtained following the method of the disclosure can be determined using well-known methods. For example, it is possible to determine the lymphocytes' capacity to provoke a marked target cell's lysis and to determine the release of the marked substance. Alternatively, the cytotoxic activity can be determined by identifying the level of cytokine (for example, GM-CSF and IFN-γ) produced by the lymphocytes or the target cell. Alternatively, the cytotoxic activity can be determined by contacting the lymphocytes with a specific antibody of cytotoxic lymphocytes marked with a first fluorescent molecule and a complex formed by the antigenic peptide and the major complex of histocompatibility marked with a second fluorescent molecule followed by the detection of cells marked with both molecules by means of flow cytometry.

The lymphocyte populations expanded according to the methods of the present disclosure are particularly useful for use in adoptive immunotherapy, in other words, for re-administering to subjects requiring a higher immune response against a specific antigen. Preferably, T lymphocytes are used autologously, in other words, are re-administered to the subject from whom they were originally extracted.

Pharmaceutical Compositions

The compositions, polynucleotides and fusion proteins of the disclosure are useful for treating diseases requiring a prolonged dose of compositions and conjugates disclosed herein. In certain embodiments, the disclosure relates to a pharmaceutical preparation comprising a therapeutically effective amount of a composition, a fusion protein, a polynucleotide, a gene construct, a vector or a host cell according to the disclosure and a pharmaceutically acceptable excipient or vehicle.

Preferred excipients for use in the present disclosure include sugars, starches, celluloses, gums and proteins. In a preferred embodiment, the pharmaceutical composition of the disclosure is formulated in a pharmaceutical form for administration as a solid (for example tablets, capsules, lozenges, granules, suppositories, crystalline or amorphous sterile solids that can be reconstituted to provide liquid forms, etc.), liquid (for example solutions, suspensions, emulsions, elixirs, lotions, unguents, etc.) or semi-solid (gels, ointments, creams and similar). The pharmaceutical compositions of the disclosure can be administered by any route, including, without limitation, oral, intravenous, intramuscular, intraarterial, intramedullary, intratecal, intraventricular, transdermic, subcutaneous, intraperitoneal, intranasal, enteric, topical, sublingual or rectal route. A revision of the different forms of administration of active principles, the excipients to be used and their manufacturing procedures can be found in the Tratado de Farmacia Galénica, C. Fauli i Trillo, Luzán 5, S. A. de Ediciones, 1993 and in Remington's Pharmaceutical Sciences (A. R. Gennaro, Ed.), 20th edition, Williams & Wilkins PA, USA (2000) Examples of pharmaceutically acceptable vehicles are known in the state of the technique and include saline solutions buffered with phosphate, water, emulsions, such as oil/water emulsions, different types of humidifying agents, sterile solutions, etc. The compositions comprising said vehicles can be formulated by conventional procedures known in the state of the technique.

Alternatively, the compositions and compounds of the disclosure can be formulated as nanolipoparticles in those cases where the composition comprises an ApoA protein or a fusion of ApoA, TGF-beta receptor, IL-15, and Sushi domain of the IL-15 receptor alpha chain or in those cases where the disclosure contemplates a fusion protein comprising TGF-beta receptor, IL-15 and the sushi domain of IL-15RA. The formation of the nanolipoparticle is based on ApoA being the major component of high density lipoproteins (HDL).

In the context of the present disclosure, the term "nanolipoparticle" is equivalent to the terms "lipoprotein" or "lipoprotein particle" which can be used indiscriminately. Nanolipoparticle is understood to mean any water-soluble particle, formed by a nucleus of apolar lipids (such as esterified cholesterol and triglycerides) covered with an external polar layer formed by apoproteins, phospholipids and free cholesterol.

Nanolipoparticles can be obtained by conventional methods known to technicians in the art. By way of illustration, the nanolipoparticles can be obtained in vitro through adding cholesterol and phosphatidylcholine to the fusion protein as described in Lerch et al. (Vox Sang, 1996, 71: 155-164) or in vivo by using a non-human animal that expresses the conjugate of the disclosure in the liver giving rise to the formation of nanolipoparticles that are secreted into serum, from where they can be isolated.

In the case of the pharmaceutical composition of the disclosure comprising nucleic acids (the polynucleotides of the disclosure, vectors or gene constructs), the disclosure contemplates specially prepared pharmaceutical compositions for administering said nucleic acids. The pharmaceutical compositions can comprise said nucleic acids in naked form, in other words, in the absence of compounds protecting the nucleic acids from degradation by the organism's nucleases, which entails the advantage of eliminating the toxicity associated to the reagents used for transfection. Suitable routes of administration for the naked compounds include intravascular, intratumoral, intracraneal, intraperitoneal, intrasplenic, intramuscular, subretinal, subcutaneous, mucous, topical and oral route (Templeton, 2002, DNA Cell Biol., 21:857-867). Alternatively, the nucleic acids can be administered forming part of liposomes, conjugated to cholesterol or conjugated to compounds capable of promoting translocation through cell membranes such as the Tat peptide derived from the TAT protein of HIV-1, the third helix of the homeodomain of the Antennapedia protein of *D.melanogaster*, the VP22 protein of the herpes simplex virus, oligomers of arginine and peptides such as those described in WO07069090 (Lindgren, A. et al., 2000, Trends Pharmacol. Sci, 21:99-103, Schwarze, S. R. et al., 2000, Trends Pharmacol. Sci., 21:45-48, Lundberg, M et al., 2003, Mol. Therapy 8:143-150 and Snyder, E. L. and Dowdy, S. F., 2004, Pharm. Res. 21:389-393). Alternatively, the polynucleotide can be administered forming part of a plasmidic vector or of a viral vector, preferably vectors based on an adenovirus, in adeno-associated viruses or in retroviruses, such as viruses based on the virus of murine leukaemia (MLV) or on lentiviruses (HIV, FIV, EIAV).

In certain embodiments, the compositions, fusion proteins and polynucleotides of the disclosure are administered by so-called "hydrodynamic administration" as described by Liu, F., et al., (Gene Ther, 1999, 6:1258-66). According to the aforesaid method, the compounds are introduced into the organism intravascularly at high speed and volume, resulting in high levels of transfection with a more widespread distribution. It has been demonstrated that the efficacy of intracellular access depends directly on the volume of fluid administered and on the speed of the injection (Liu et al., 1999, Science, 305:1437-1441). In mice, the administration has been optimised to values of 1 ml/10 g of body weight over a period of 3-5 seconds (Hodges et al., 2003, Exp. Opin. Biol. Ther, 3:91-918). The exact mechanism that allows cellular transfection in vivo with polynucleotides following their hydrodynamic administration is not entirely known. In the case of mice, it is believed that administration by the tail vein occurs at a higher rhythm than the heart beat, provoking the administered fluid to accumulate in the superior vena cava. This fluid subsequently accesses the organ's vessels and, subsequently, through fenestration in the aforesaid vessels, accesses the extravascular space. In this way, the polynucleotide comes into contact with the cells of the target organ before mixing with the blood thereby reducing the possibilities of degradation by nucleases.

The compositions of the disclosure can be administered at doses of less than 10 mg per kilogram of body weight, preferably less than 5, 2, 1, 0.5, 0.1, 0.05, 0.01, 0.005, 0.001, 0.0005, 0.0001, 0.00005 or 0.00001 mg per each kg of body weight and less than 200 nmol of agent, in other words, approximately $4.4 \times 1016$ copies per kg of body weight or less than 1500, 750, 300, 150, 75, 15, 7.5, 1.5, 0.75, 0.15 or 0.075 nmol per Kg of body weight. The unitary dose can be administered by injection, by inhalation or by topical administration. The bifunctional polynucleotides and compositions of the disclosure can be administered directly into the organ in which the target mRNA is expressed in which case doses will be administered of between 0.00001 mg and 3 mg per organ, or preferably between 0.0001 and 0.001 mg per organ, about 0.03 and 3.0 mg per organ, about 0.1 and 3.0 mg per organ or between 0.3 and 3.0 mg per organ.

The dose will depend on the severity and response to the condition to be treated and may vary between several days and several months or until the condition is seen to remit. The optimum dose can be determined by periodically measuring the agent's concentrations in the patient's organism. The optimum dose can be determined from the EC50 values obtained through previous in vitro or in vivo tests in animal models. The unitary dose can be administered once a day or less than once a day, preferably, less than once every 2, 4, 8 or 30 days. Alternatively, it is possible to administer an initial dose followed by one or several maintenance doses, generally in a lesser amount that the initial dose. The maintenance regime may involve treating the patient with doses ranging between 0.01 µg and 1.4 mg/kg of body weight per day, for example 1, 0.1, 0.01, 0.001, or 0.00001 mg per kg of body weight per day. Maintenance doses are administered, preferably, at most once every 5, 10 or 30 days. The treatment must continue for a time that will vary according to the type of alteration suffered by the patient, its severity and the patient's condition. Following treatment, the patient's evolution must be monitored in order to determine whether the dose ought to be increased in the case of the disease not responding to the treatment or whether the dose ought to be decreased in the case of observing an improvement in the disease or unwanted secondary effects.

The daily dose can be administered in a single dose or in two or more doses according to the particular circumstances. If a repeated administration or frequent administrations are required, it is advisable to implant an administration device, such as a pump, a semi-permanent catheter (intravenous, intraperitoneal, intracisternal or intracapsular) or a reservoir.
Therapeutic Uses of the Compositions and Conjugate Proteins In certain embodiments, the disclosure relates also to the compositions, conjugates, fusion proteins and polynucleotides of the disclosure for use in medicine.

The capacity of IL-15 to promote NK cell activity allows to use of the conjugates and compositions of the disclosure to treat patients who can benefit from stimulation of the innate (NK cell-mediated) or adaptive (CD8 lymphocyte-mediated) immune response.

In certain embodiments, the disclosure relates to a composition of the disclosure, a fusion protein of the disclosure, a polynucleotide of the disclosure, a vector or a gene construct of the disclosure, or a host cell of the disclosure for use in stimulating an immune response in a subject.

Preferably, the composition of the disclosure, fusion protein of the disclosure, polynucleotide of the disclosure, vector or gene construct of the disclosure, or host cell of the disclosure are used to treat a disease that requires activation of the immune system in response to an antigen.

In certain embodiments, the disclosure relates to the use of a composition of the disclosure, a fusion protein of the disclosure, a polynucleotide of the disclosure, a vector or a gene construct of the disclosure, or a host cell of the disclosure for the manufacture of a medicament for stimulating a subject's immune response to an antigen or to treat a disease requiring activation of the immune system.

Alternatively, the disclosure relates to a method for promoting the stimulation of an immune response to an antigen or for treating a disease requiring activation of the immune system which comprises the administration to said subject of a composition of the disclosure, a fusion protein of the disclosure, a polynucleotide of the disclosure, a vector or a gene construct of the disclosure, or a host cell of the disclosure.

The expression "stimulation of a subject's immune response", as used in the present disclosure, refers to the initiation of an immune response against a specific antigen in an individual wherein said response occurs for the first time as well as to the reactivation of the immune response in subjects wherein said immune response has already occurred. It is understood that the immune response can involve both the innate as well as the adaptive immune response, and can involve either a humoral or cellular-type response.

Therefore, the capacity of the compounds and compositions of the disclosure to increase a subject's immune response to a specific antigen can be useful for treating diseases associated to the presence of said antigen in the organism, which includes diseases caused by viral infections if dealing with a viral antigen, diseases caused by bacterial infections if dealing with a bacterial antigen, diseases caused by fungal infections if dealing with a fungal antigen, allergies if dealing with an allergen, diseases caused by a parasitic infestation if dealing with a parasitic antigen and/or a tumor if dealing with a tumor cell specific antigen. Therefore, in preferred embodiments, the disease requiring activation of the immune system is selected from the group of an infectious disease and a neoplastic disease.

Diseases caused by viral infections that can be treated using the compounds and combinations of the disclosure include, without limitation, diseases caused by infections with the HIV-1 virus (AIDS), by the human herpes virus such as the simple herpes virus (simple herpes, genital herpes), cytomegalovirus (mononucleosis, retinitis, hepatitis), the Epstein Barr virus (infectious mononucleosis, Burkitt's lymphoma and nasopharyngeal carcinoma) and the virus of varicella zoster (chickenpox, herpes zoster); by hepatitis viruses such as hepatitis B virus or hepatitis C virus, by paramyxovirus such as respiratory syncytial virus, the parainfluenza virus, rubella virus, measles virus, mumps virus, human papillomavirus; flavivirus such as the yellow fever virus, dengue fever virus, the virus of tick-transmitted encephalitis or the Japanese encephalitis virus) and rotavirus. Other types of viral infections that can be treated using the compounds and combinations of the present disclosure are described in detail in Fundamental Virology, second edition, eds. Fields, B. N. and Knipe, D. M. (Raven Press, New York, 1991).

Diseases caused by bacterial infections that can be treated using the compounds and combinations of the disclosure include, without limitation, diseases caused by microorganisms of the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus* or *Bordetella.*

Diseases caused by fungal infections that can be treated using the compounds and combinations of the disclosure include, without limitation, candidiasis, aspergillosis, histoplasmosis, cryptococcal meningitis and similar.

Parasitic infections that can be treated using the compounds and combinations of the disclosure include, without limitation, malaria, infection by *Pneumocystis jiroveci*, pneumonia, sleeping sickness, leishmaniosis, cryptosporidiosis, toxoplasmosis and *trypanosoma.*

Allergic-type disorders that can be treated using the compounds and compositions of the disclosure include, without limitation, allergies caused by exposure to pollen (allergens of pollen from trees, herbs, weeds, and grasses), allergies caused by exposure to insect allergens (inhalable allergens, allergens from saliva, and poison), dandruff and animal hair allergens and food allergens.

The conjugates and compositions of the disclosure are also suitable for treating hyperproliferative diseases. The expression "proliferative disease", as used in the present disclosure, refers to diseases caused by or resulting from inappropriately high levels of cell division, inappropriately low levels of apoptosis or both and include both primary tumors as well as metastases. The term "primary tumor" refers to a tumor in the primary site where the tumor originated. The term "metastasis", as used in the present disclosure, refers to the process whereby a tumor extends to organism tissues other than those of the tumor's original primary site.

In the context of the disclosure, "treatment of a hyperproliferative disease" or "treatment of a tumor" is understood to mean the administration of the compounds and compositions of the disclosure in order to prevent or delay the appearance of symptoms, complications, or biochemical indications of the cancer or tumor, to alleviate its symptoms or to prevent or inhibit its growth and progression such as, for example, the appearance of metastasis. The treatment may be a prophylactic treatment to delay the appearance of the disease or to prevent the manifestation of its clinical or sub-clinical symptoms or a therapeutic treatment to eliminate or alleviate symptoms after manifestation of the disease or in relation to its treatment through surgery or radiotherapy.

The cancer to be treated in the context of the present disclosure may be any type of cancer or tumor. These tumors or cancer include, and are not limited to, malignancies located in the colon, abdomen, bone, breast, digestive system, liver, pancreas, peritoneum, endocrine glands (adrenal, parathyroid, hypophysis, testicles, ovaries, thymus, thyroid), eye, head and neck, nervous system (central and peripheral), lymphatic system, pelvis, skin, soft tissue, spleen, thorax and genito-urinary apparatus and, more particularly, childhood acute lymphoblastic leukaemia, acute lymphoblastic leukaemia, acute lymphocytic leukaemia, acute myeloid leukaemia, adrenocortical carcinoma, adult (primary) hepatocellular cancer, adult (primary) liver cancer, adult acute lymphocytic leukaemia, adult acute myeloid leukaemia, adult Hodgkin's disease, adult Hodgkin's lymphoma, adult lymphocytic leukaemia, adult non-Hodgkin's lymphoma, adult primary liver cancer, adult soft tissue sarcoma, AIDS-related lymphoma, AIDS-related malignant tumors, anal cancer, astrocytoma, cancer of the biliary tract, cancer of the bladder, bone cancer, brain stem glioma, brain tumors, breast cancer, cancer of the renal pelvis and ureter, primary central nervous system lymphoma, central nervous system lymphoma, cerebellar astrocytoma, brain astrocytoma, cancer of the cervix, childhood (primary) hepatocellular cancer, childhood (primary) liver cancer, childhood acute lymphoblastic leukaemia, childhood acute myeloid leukaemia, childhood brain stem glioma, childhood cerebellar astrocytoma, childhood brain astrocytoma, childhood extracranial germ cell tumors, childhood Hodgkin's disease, childhood Hodgkin's lymphoma, childhood visual pathway and hypothalamic glioma, childhood lymphoblastic leukaemia, childhood medulloblastoma, childhood non-Hodgkin's lymphoma, childhood supratentorial primitive neuroectodermal and pineal tumors, childhood primary liver cancer, childhood rhabdomyosarcoma, childhood soft tissue sarcoma, childhood visual pathway and hypothalamic glioma, chronic lymphocytic leukaemia, chronic myeloid leukaemia, cancer of the colon, cutaneous T-cell lymphoma, endocrine pancreatic islet cells carcinoma, endometrial cancer, ependymoma, epithelial cancer, cancer of the oesophagus, Ewing's sarcoma and related tumors, cancer of the exocrine pancreas, extracranial germ cell tumor, extragonadal germ cell tumor, extrahepatic biliary tract cancer, cancer of the eye, breast cancer in women, Gaucher's disease, cancer of the gallbladder, gastric cancer, gastrointestinal carcinoid tumor, gastrointestinal tumors, germ cell tumors, gestational trophoblastic tumor, tricoleukaemia, head and neck cancer, hepatocellular cancer, Hodgkin's disease, Hodgkin's lymphoma, hypergammaglobulinemia, hypopharyngeal cancer, intestinal cancers, intraocular melanoma, islet cell carcinoma, islet cell pancreatic cancer, Kaposi's sarcoma, cancer of kidney, cancer of the larynx, cancer of the lip and mouth, cancer of the liver, cancer of the lung, lymphoproliferative disorders, macroglobulinemia, breast cancer in men, malignant mesothelioma, malignant thymoma, medulloblastoma, melanoma, mesothelioma, occult primary metastatic squamous neck cancer, primary metastatic squamous neck cancer, metastatic squamous neck cancer, multiple myeloma, multiple myeloma/plasmatic cell neoplasia, myelodysplastic syndrome, myelogenous leukaemia, myeloid leukaemia, myeloproliferative disorders, paranasal sinus and nasal cavity cancer, nasopharyngeal cancer, neuroblastoma, non-Hodgkin's lymphoma during pregnancy, non-melanoma skin cancer, non-small cell lung cancer, metastatic squamous neck cancer with occult primary, buccopharyngeal cancer, malignant fibrous osteosarcoma-Z, osteosarcoma-W, malignant fibrous histiocytoma, malignant fibrous osteosarcoma/histiocytoma of the bone, epithelial ovarian cancer, ovarian germ cell tumor, ovarian low malignant potential tumor, pancreatic cancer, paraproteinemias, purpura, parathyroid cancer, cancer of the penis, phaeochromocytoma, hypophysis tumor, neoplasia of plasmatic cells/multiple myeloma, primary central nervous system lymphoma, primary liver cancer, prostate cancer, rectal cancer, renal cell cancer, cancer of the renal pelvis and ureter, retinoblastoma, rhabdomyosarcoma, cancer of the salivary glands, sarcoidosis, sarcomas, Sezary's syndrome, skin cancer, small cell lung cancer, small intestine cancer, soft tissue sarcoma, squamous neck cancer, stomach cancer, pineal and supratentorial primitive neuroectodermal tumors, T-cell lymphoma, testicular cancer, thymoma, thyroid cancer, transitional cell cancer of the renal pelvis and ureter, transitional renal pelvis and ureter cancer, trophoblastic tumors, cell cancer of the renal pelvis and ureter, cancer of the urethra, cancer of the uterus, uterine sarcoma, vaginal cancer, optic pathway and hypothalamic glioma, cancer of the vulva, Waldenstrom's macroglobulinemia, Wilms' tumor and any other hyperproliferative disease, as well as neoplasia, located in the system of a previously mentioned organ.

Vaccine Compositions

The conjugates and compositions of the disclosure are useful also as adjuvants in vaccines to increase a patient's response to an antigen. Thus, in certain embodiments, the disclosure relates to a vaccine composition comprising an antigen and a composition, fusion protein, polynucleotide, gene construct, vector or host cell according to the disclosure.

The term "vaccine" or "vaccine composition", as used in the present disclosure, refers to a composition comprising at least one antigen of interest that allows activation of a subject's immune response to said antigen. The purpose of the vaccines is to activate immunity mediated by both cells as well as antibodies. Preferably, cell-mediated immunity includes the stimulation of a T-cell response, mainly, a response mediated by CD4+, and/or a response of CD8+ T cells.

The term "adjuvant", as used in the present disclosure, refers to an immunological agent capable of activating the immune system allowing a more intense and more efficient immune response to a vaccine than would be obtained as a result of administering the vaccine without the adjuvant. Typical responses to adjuvants include, without limitation, the activation, proliferation and/or differentiation of immune system cells (B cells, T cells, dendritic cells, antigen-presenting cells, macrophages, NK cells), the increased or decreased expression of markers and cytokines, the stimulation of IgA, IgM and/or IgG titres, splenomegalia (increase in spleen cellularity), hyperplasia, the formation of infiltrates in different organs and other types of responses that can be quantified by an expert in the art using standard technology.

Thus, the vaccines that can be used in combination with the combinations and compounds of the disclosure include vaccines presenting one or more antigens selected from the group of a viral antigen, bacterial antigens, a fungal antigen, an allergen or an environmental antigen and a tumoral antigen.

Viral antigens suitable for use in the vaccines that can be used with the compounds and combinations of the disclosure include HIV-1 antigens (such as tat, nef, gp120 or gp160, gp40, p24, gag, env, vif, vpr, vpu, rev), human herpes viruses, (such as gH, gL gM gB gC gK gE or gD or derivatives thereof) or immediate early protein such as ICP27, ICP47, ICP4, ICP36 of VHS1 or VHS2, cytomegalovirus, especially human, (such as gB or derivatives thereof), Epstein Barr viruses (such as gp350 or derivatives thereof), viruses of varicella zoster (such as gpl, II, III and IE63), or a virus of hepatitis such as the hepatitis B virus (for example surface antigen of hepatitis B or nucleus antigen of hepatitis), hepatitis C virus (for example nucleus antigens, E1, NS3 or NS5), of paramyxovirus such as respiratory syncytial virus (such as proteins F and G or derivatives thereof), of the parainfluenza virus, of the measles virus (such as proteins EI and E2), chickenpox virus, mumps virus, human papillomavirus (for example HPV6, 11, 16, 18, eg LI, L2, EI, E2, E3, E4, E5, E6, E7), flavivirus (for example the virus of yellow fever, dengue fever virus, virus of tick-transmitted encephalitis, Japanese encephalitis virus) or cells infected with influenza viruses, such as proteins HA, NP, NA or M, or combinations thereof), antigens of rotavirus (such as VP7sc and other rotavirus components), and similar (see Fundamental Virology, second edition, eds. Fields, B. N. and Knipe, D. M. (Raven Press, New York, 1991) for additional examples of viral antigens.

Bacterial antigens or derivatives suitable for use in the vaccines that can be used with the compounds and combinations of the disclosure include antigens of *Neisseria* spp, including N. gonorrhea and *N. meningitidis* (transferrin binding proteins, lactoferrin binding proteins, PiIC and adhesins); antigens of *S. pyogenes* (such as M proteins or fragments thereof and C5A protease); antigens of *S. agalactiae, S. mutans; H. ducreyi; Moraxella* spp, including *M catarrhalis*, also known as *Branhamella catarrhalis* (such as low and high molecular weight adhesins and invasins); antigens of *Bordetella* spp, including *B. pertussis* (for example *Parapertussis* and *B. bronchiseptica* (such as pertactin, the whooping cough toxin or derivatives thereof, filamentous hemagglutinin, adenylate cyclase, fimbriae); antigens of *Mycobacterium* spp., including *M. tuberculosis, M. bovis, M. leprae, M. avium, M. paratuberculosis, M. smegmatis; Legionella* spp, including *L. pneumophila*; (for example ESAT6, antigen 85A, —B or —C, MPT 44, MPT59, MPT45, HSPIO, HSP65, HSP70, HSP 75, HSP90, PPD of 19 kDa [Rv3763], PPD of 38 kDa [Rv0934]); antigens of *Escherichia* spp, including enterotoxigenic *E. coli* (for example colonisation factors, thermolabile toxin or derivatives thereof, thermostable toxin or derivatives thereof), antigens of enterohaemorrhagic *E. coli* and enteropathogenic *E. coli* (for example toxin similar to the Shiga-toxin or derivatives thereof); antigens of *Vibrio* spp, including *V. cholera* (for example cholera toxin or derivatives thereof); antigens of *Shigella* spp, including *S. sonnei, S. dysenteriae*, S. flexnerii; *Yersinia* spp, including *Y. enterocolitica* (for example a Yop protein); antigens of *Y. pestis, Y. pseudotuberculosis; Campylobacter* spp, including *C. jejuni* (for example toxins, adhesins and invasins); antigens of *Salmonella* spp, including *S. typhi, S. paratyphi, S. choleraesuis, S. enteritidis; Listeria* spp., including *L. monocytogenes; Helicobacter* spp, including *H. pylori* (for example urease, catalase, vacuolating toxin); antigens of *Pseudomo-* nas spp, including *P. aeruginosa; Staphylococcus* spp., including *S. aureus, S. epidermidis; Enterococcus* spp., including *E. faecalis, E. faecium; Clostridium* spp., including *C. tetani* (for example tetanic toxin and derivative thereof); antigens of *C. botulinum* (for example botulinic toxin and derivative thereof), antigens of *C. difficile* (for example toxins of *clostridium* A or B and derivatives thereof); antigens of *Bacillus* spp., including *B. anthracis* (for example the anthrax toxin and derivatives thereof); *Corynebacterium* spp., including *C. diphtheriae* (for example diphtheria toxin and derivatives thereof); antigens of *Borrelia* spp., including *B. burgdorferi* (for example OspA, OspC, DbpA, DbpB); antigens of *B. garinii* (for example OspA, OspC, DbpA, DbpB), *B. afzelii* (for example OspA, OspC, DbpA, DbpB), antigens of B. andersonfi (for example OspA, OspC, DbpA, DbpB), antigens of *B. hermsii; Ehrlichia* spp., including *E. equi* and the agent of human granulocytic ehrlichiosis; *Rickettsia* spp, including *R. rickettsii; Chlamydia* spp., including *C. trachomatis* (for example MOMP, heparin-binding proteins); antigens of *Chlamydia pneumoniae* (for example MOMP, heparin-binding proteins), antigens of *C. psittaci; Leptospira* spp., including *L. interrogans; Treponema* spp., including *T. pallidum* (for example rare outer membrane proteins), antigens of *T. denticola, T. hyodysenteriae*; antigens of *Plasmodium* spp., including *P. falciparum; Toxoplasma* spp. and *T. gondii* (for example SAG2, SAGS, Tg34); antigens of *Entamoeba* spp., including *E. histolytica; Babesia* spp., including *B. microti; Trypanosoma* spp., including *T. cruzi; Giardia* spp., including *G. lamblia; leishmania* spp., including *L. major; Pneumocystis* spp., including *P. carinii; Trichomonas* spp., including *T. vaginalis; Schisostoma* spp., including *S. Mansoni.*

Antigens of or derived from yeast such as *Candida* spp., including *C. albicans; Cryptococcus* spp., including *C. neoformans*; antigens of *M. tuberculosis* (such as Rv2557, Rv2558, RPFs: Rv0837c, Rv1884c, Rv2389c, Rv2450, Rv1009, aceA (Rv0467), PstS1, (Rv0932), SodA (Rv3846), Rv2031c of 16 kDal, Tb Ra12, Tb H9, Tb Ra35, Tb38-1, Erd 14, DPV, MTI, MSL, mTTC2 and hTCC1); antigens of *Chlamydia*, such as high molecular weight protein (HMWP), ORF3 (document EP 366 412) and possible membrane proteins (Pmp); antigens of *Streptococcus* spp, including *S. pneumoniae* (PsaA, PspA, streptolysin, choline binding proteins, the protein antigen pneumolysin, and mutant detoxified derivatives thereof); antigens derived from *Haemophilus* spp., including *H. influenzae* type B (for example PRP and conjugates thereof); antigens of unclassifiable *H. influenzae* (such as OMP26, high molecular weight adhesins, P5, P6, protein D and lipoprotein D, and fimbrin and fimbrin derived peptides, or variants of multiple copies or the fusion proteins thereof); antigens derived from *Plasmodium falciparum* (such as RTS.S, TRAP, MSP1, AMA1, MSP3, EBA, GLURP, RAP1, RAP2, sequestrin, PfEMP1, Pf332, LSA1, LSA3, STARP, SALSA, PfEXP1, Pfs25, Pfs28, PFS27/25, Pfs16, Pfs48/45, Pfs230 and analogues thereof in *Plasmodium* spp.)

Fungal antigens suitable for use in the vaccines that can be used with the compounds and combinations of the disclosure include, without limitation, for example, components of the fungal antigen of *Candida*; fungal antigens of *Histoplasma* such as heat shock protein 60 (HSP60) and other components of fungal antigens of *Histoplasma*; fungal antigens of *cryptococcus* such as capsular polysaccharides and other components of fungal antigens of *cryptococcus*; fungal antigens of coccidia such as antigens of spherula and other components of fungal antigens of coccidia; and fungal antigens of Tinea such as trichophytin and other components of fungal antigens of coccidia.

Protozoan antigens suitable for use in the vaccines that can be used with the compounds and combinations of the disclosure include, without limitation, antigens of *Plasmodium falciparum* such as merozoite surface antigens, sporozoite surface antigens, circumsporozoite antigens, gametocyte/gamete surface antigens, whole blood antigen pf, 55/RESA and other components of plasmoid antigens; antigens of *Toxoplasma* such as SAG-I, p30 and other components of *Toxoplasma* antigens; antigens of *schistosoma* such as glutation-S-transferase, paramyosin and other components of the *schistosoma* antigen; the antigen of *Leishmania* and other antigens of *Leishmania* tales such as gp63, lipophosphoglycan and its associated protein and other components of the *Leishmania* antigen; and antigens of *Trypanosoma cruzi* such as the antigen of 75-77 kDa, the antigen of 56 kDa and other components of the *Trypanosoma* antigen.

Allergens or environmental antigens suitable for use in the vaccines that can be used with the compounds and combinations of the disclosure include, without limitation, antigens derived from naturally-produced allergens such as pollen allergens (allergens of the pollen from trees, herbs, weeds and grasses), insect allergens (inhalable allergens, from saliva and poison), dandruff and animal hair allergens, and food allergens. Important pollen allergens from trees, grasses and herbs originate from taxonomic orders of Fagales, Oleales, Pinales and Platanaceae including among others birch (*Betula*), alder (*Alnus*), hazel nut tree (*Corylus*), hornbeam (*Carpinus*) and olive (*Olea*), cedar (*Cryptomeria* and *Juniperus*), banana tree (*Platanus*), the order of Poales including among others grasses of the genera *Lolium, Phleum, Poa, Cynodon, Dactylis, Holcus, Phalaris, Secale* and Sorghum, the orders of Asterales and Urticales including among others herbs of the genera *Ambrosia, Artemisia* and *Parietaria*. Other allergenic antigens that can be used include the allergens of household dust mites of the genera *Dermatophagoides* and Euroglyphus, storage mites for example Lepidoglyphys, Glycyphagus and Tyrophagus, those of cockroaches, midges and fleas for example Blatella, *Periplaneta*, Chironomus and Ctenocepphalides, those of mammals such as cat, dog and horse, birds, poison allergens including those originating from insect stings or bites such as those of the taxonomic order of Hymenoptera including bees (superfamily Apidae), wasps and ants (superfamily Formicoidae). Yet more allergenic antigens that can be used include inhaled fungal allergens such as from the genera *Alternaria* and *Cladosporium*.

Tumoral antigens suitable for use in the vaccines that can be used with the compounds and combinations of the disclosure include, without limitation, MAGE, MART-1/ Melan-A, gp100, dipeptidyl peptidase IV (DPPIV), adenosine deaminase binding protein (ADAbp), cyclophilin b, colorectal associated antigen (CRC)-0017-1A/GA733, carcinoembrionary antigen (CEA) and its antigenic epitopes CAP-1 and CAP-2, etv6, aml1, prostate specific antigen (PSA) and its antigenic epitopes PSA-1, PSA-2, and PSA-3, prostate specific membrane antigen (PSMA), T-cell/CD3-c chain receptor, MAGE family of tumor antigens (for example, MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE family of tumor antigens (for example, GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p2Iras, RCAS1, α-foetoprotein, E-cadherin, α-catenin, 13-catenin, γ-catenin, p12Octn, gp100Pme1117, PRAME, NY-ESO-1, cdc27, adenomatous polyposis of the colon protein (APC), fodrin, Connexin 37, idiotype Ig, p15, gp75, GM2 and GD2 gangliosides, viral products such as the proteins of the human papillomavirus, Smad family of tumor antigens, Imp-1, PIA, EBV encoded nuclear antigen (EBNA)-1, brain glycogen phosphorylase, SSX-1, SSX-2 (HOM-MEL-40), SSX-3, SSX-4, SSX-5, SCP-1 and CT-7, and c-erbB-2, acute lymphoblastic leukaemia (etv6, amII, cyclophilin b), B cell lymphoma (idiotype Ig), glioma (E-cadherin, a-catenin, 13-catenin, 7-catenin, p120ctn), bladder cancer (p2Iras), biliary cancer (p2Iras), breast cancer (MUC family, HER2/neu, c-erbB-2), carcinoma of the cervix (p53, p2Iras), carcinoma of the colon (p2Iras, HER2/neu, c-erbB-2, MUC family), colorectal cancer (colorectal associated antigen (CRC)-0017-1A/GA733, APC), choriocarcinoma (CEA), epithelial cell cancer (cyclophilin b), gastric cancer (HER2/neu, c-erbB-2, ga733 glycoprotein), hepatocellular cancer, Hodgkin's lymphoma (Imp-1, EBNA-1), lung cancer (CEA, MAGE-3, NY-ESO-1), lymphoid cell-derived leukaemia (cyclophilin b), melanoma (p15 protein, gp75, oncofetal antigen, GM2 and GD2 gangliosides, Melan-A/MART-1, cdc27, MAGE-3, p2Iras, gp100Pme1117), myeloma (MUC family, p2Iras), non-small cell lung cancer (HER2/neu, c-erbB-2), nasopharyngeal cancer (Imp-1, EBNA-1), ovarian cancer (MUC family, HER2/neu, c-erbB-2), prostate cancer (prostate specific antigen (PSA) and its antigenic epitopes PSA-1, PSA-2 and PSA-3, PSMA, HER2/neu, c-erbB-2, ga733 glycoprotein), renal cancer (HER2/neu, c-erbB-2), squamous cell cancers of the cervix and oesophagus (viral products such as human papillomavirus proteins), testicular cancer (NY-ESO-1) and T-cell leukaemia (HTLV-1 epitopes).

The components of the compositions of the disclosure, specifically, the fusion of TGF-beta receptor and IL-15 or the polynucleotide encoding said fusion and the Sushi domain of the IL-15 receptor alpha chain or the nucleic acid encoding said domain can be presented as a single formulation (for example, as a tablet or capsule comprising a fixed amount of each component) or, otherwise, can be presented as separate formulations for subsequent combination for joint, sequential or separate administration. The compositions of the disclosure also contemplate the formulation as a kit of parts wherein the components are formulated separately but are packaged in the same container.

The expert in the art will appreciate that the formulation of the first and second component of the compositions of the disclosure can be similar, in other words, formulated in a similar way (for example, in tablets or in pills), allowing administration by the same route. In an embodiment wherein the different components of the disclosure are formulated separately, the two components can be presented in a blister pack. Each blister will contain the medicaments to be consumed throughout the day. If the medicaments need to be administered several times a day, the medicaments corresponding to each administration can be arranged in separate sections of the blister pack, preferably noting on each section of the blister pack the time of day when they need to be administered. Alternatively, the components of the composition of the disclosure can be formulated in a different manner so that the different components are administered differently. Thus, it is possible, for example, for the first component to be formulated as a tablet or capsule for oral administration and for the second component to be formulated for intravenous administration.

The compositions of the disclosure are administered according to methods known to an expert in the art, including, without limitation, intravenous, oral, nasal, parenteral, topical, transdermic, rectal and similar.

The disclosure is described below through the following examples which are purely illustrative and not limitative of the scope of the disclosure.

EXAMPLES

FIST-15 is Produced by Using Mammalian Expression Systems

Transient chemical transfection: A DNA plasmid containing the cDNA for FIST-15 is chemically transfected (QIAGEN PolyFect) into HEK-293T cells. Conditioned media from transfected cells are harvested 30-40 hours post-transfection and concentrated before protein quantification via ELISA.

Stable transduction: DNA plasmid encoding the FIST-15 cDNA is chemically transfected together with a pVSV-G plasmid into 293-GP2 cells, a viral packaging cell line. Retroviruses containing the FIST-15 cDNA bearing plasmid are then used to infect HEK-293T cells or B16 melanoma cells. FIST-15 cDNA is permanently integrated into the cellular genome of these cells. HEK-293T cells may be infected with virus 1-3×. Positive single clones (assayed by GFP expression, also contained on the plasmid) are selected and propagated. Conditioned media from expanded single clones are concentrated before protein quantification via ELISA. B16 cells stably transduced to express FIST-15 may be used for experiments that determine the effect of locoregional FIST-15 secretion.

```
Murine FIST-15
                                  (SEQ ID NO: 24)
HHHHHHHHENLYFQGSIPPHVPKSVNSDVMASDNGGAVKLPQLCKFCDVR

LSTCDNQKSCMSNCSITAICEKPHEVCVAVWRKNDKNITLETVCHDPKLT

YHGFTLEDAASPKCVMKEKKRAGETFFMCACNMEECNDYIIFSEEYTTSS

PDIPPHVPKSVNSDVMASDNGGAVKLPQLCKFCDVRLSTCDNQKSCMSNC

SITAICEKPHEVCVAVWRKNDKNITLETVCHDPKLTYHGFTLEDAASPKC

VMKEKKRAGETFFMCACNMEECNDYIIFSEEYTTSSPDGTGGSSGGTTCP

PPVSIEHADIRVKNYSVNSRERYVCNSGFKRKAGTSTLIECVINKNTNVA

HWTTPSLKCIRDPSLAHYSPVPSGGSGGGGSGGGSGGGGSLQNWIDVRYD

LEKIESLIQSIHIDTTLYTDSDFHPSCKVTANINCFLLELQVILHEYSNM

TLNETVRNVLYLANSTLSSNKNVAESGCKECEELEEKTFTEFLQSFIRIV

QMFINTS
```

The FIST-15 protein is composed on an 8×-His-Tag immediately followed by a tobacco etch virus (TEV) protease cleavage site. These two domains allow for purification of the protein. Two extracellular domains of the TGF-β receptor (type II) are linked in tandem to one another (no linker). Following these two receptor domains is a KpnI restriction enzyme site (encoded as GT), which allows for the swapping in of other cytokines immediately C'- of the TGF-beta receptors. This construct contains a restriction enzyme site for the swapping of different interleukins in place of IL-15. Proceeding the KpnI site is a short polyglycine/serine linker (GGSSGG) (SEQ ID NO: 13), followed by the minimally defined IL-15Rα sushi domain. A longer poly-glycine/serine linker (SGGSGGGGSGGGSGGGGSLQ) (SEQ ID NO: 14) bridges the sushi domain with mature IL-15.

The sushi domain of the IL-15Rα is a 65 amino acid long region of the receptor that is known to interact with IL-15. IL-15Rα has a much higher affinity for IL-15 than does the IL-2Rα (CD25) for IL-2 (Kd $10^{-11}$M vs. Kd $10^{-8}$M). Disruption of residues in the sushi domain by site-directed mutagenesis alters its binding ability to IL-15. A description of the IL-15Rα sushi domain was first published in 2001 by Wei et al. (J. Immunol. 2001 Jul. 1; 167(1):277-82). IL-15Rα is produced as a chaperone protein with IL-15 and is presented in trans to IL-2/15Rβ-chain (CD122) and common gamma chain (γ-c, CD132) expressing cells (i.e. the low affinity IL-15 receptor).

An alternative FIST-15 protein is

```
                                     (SEQ ID NO: 25)
MNFLLSWVHWSLALLLYLHHAKWSQAENLYFQSHHHHHHHHIPPHVPKS

VNSDVMASDNGGAVKLPQLCKFCDVRLSTCDNQKSCMSNCSITAICEKP

HEVCVAVWRKNDKNITLETVCHDPKLTYHGFTLEDAASPKCVMKEKKRA

GETFFMCACNMEECNDYIIFSEEYTTSSPDIPPHVPKSVNSDVMASDNG

GAVKLPQLCKFCDVRLSTCDNQKSCMSNCSITAICEKPHEVCVAVWRKN

DKNITLETVCHDPKLTYHGFTLEDAASPKCVMKEKKRAGETFFMCACNM

EECNDYIIFSEEYTTSSPDGTGGSSGGTTCPPPVSIEHADIRVKNYSVN

SRERYVCNSGFKRKAGTSTLIECVINKNTNVAHWTTPSLKCIRDPSLAH

YSPVPSGGSGGGGSGGGSGGGGSLQNWIDVRYDLEKIESLIQSIHIDTT

LYTDSDFHPSCKVTAMNCFLLELQVILHEYSNMTLNETVRNVLYLANST

LSSNKNVAESGCKECEELEEKTFTEFLQSFIRIVQMFINTS.
```

```
FIST-15 human ortholog
                                     (SEQ ID NO: 26)
HHHHHHHHHENLYFQGSTIPPHVQKSVNNDMIVTDNNGAVKFPQLCKFCD

VRFSTCDNQKSCMSNCSITSICEKPQEVCVAVWRKNDENITLETVCHDP

KLPYHDFILEDAASPKCIMKEKKKPGETFFMCSCSSDECNDNIIFSEEY

NTSNPDTIPPHVQKSVNNDMIVTDNNGAVKFPQLCKFCDVRFSTCDNQK

SCMSNCSITSICEKPQEVCVAVWRKNDENITLETVCHDPKLPYHDFILE

DAASPKCIMKEKKKPGETFFMCSCSSDECNDNIIFSEEYNTSNPDGTGG

SSGITCPPPMSVEHADIWVKSYSLYSRERYICNSGFKRKAGTSSLTECV

LNKATNVAHWTTPSLKCIRDPALVHQRPAPPSGGSGGGGSGGGSGGGGS

LQNWVNVISDLKKIEDLIQSMHIDATLYTESDVHPSCKVTAMKCFLLEL

QVISLESGDASIHDTVENLIILANNSLSSNGNVTESGCKECEELEEKNI

KEFLQSFVHIVQMFINTS.
```

First underlined portion (following the N-terminus, polyhistidine) contains a once repeated human TGF-beta receptor (Type II) ectodomain sequence. The second underlined portion is human IL-15 receptor alpha sushi domain, and the third underlined portion is a mature human IL-15 sequence. The first and second underlined portions are separated by a KpnI restriction enzyme site and a first linker. The second and third underlined portions are separated by a second linker.

FIST15 Enhances NK Cell Effector Molecule Expression and Augments In Vitro Cytolysis of B16-F0 Melanoma and MC-38 Colon Adenocarcinoma Cells Similar to CD8+ T cells, FIST15 treated NK cells also displayed significantly increased production of IFNγ compared to control treated NK cells, upon PMA and ionomycin stimulation. Absolute numbers of NK cells secreting IFNγ, TNFα, or IL2 were also significantly increased compared to control cytokine treatment. To test whether FIST15 stimulated NK cells could inhibit tumor growth in vitro, the murine B16-F0 melanoma cell line, transduced to express GFP (B16-GFP), was utilized in a cytolytic assay. B16-GFP cells were allowed to adhere overnight before being placed in co-culture with murine NK cells for 48 hours at increasing concentrations of FIST15 or control cytokines. Adherent B16-GFP cells were then trypsinized and analyzed by flow cytometry for GFP+ events. While FIST15 had no direct effect on B16-GFP growth, NK cells in the presence of FIST15 significantly diminished B16-GFP growth. Using non-linear regression, a concentration of FIST15 or IL15 and sTβRII required to inhibit 50% of B16-GFP growth (IC50) could be determined. Compared to treatment with equimolar IL15 and sTβRII treated NK cells, FIST15 achieved an IC50 approximately 6-fold lower (1.27 pM, FIST15 vs 7.52 pM, IL15+sTβRII) suggesting it is more potent at stimulating NK cell cytolysis of B16-F0 melanoma in vitro. Low or lack of MHC-I expression on target tumor cells has been known to spontaneously induce NK cell-mediated cytolysis.

In order to test whether FIST15 could stimulate NK cells to lyse MHC-I expressing cells, syngeneic MC-38 colon adenocarcinoma cells were utilized. MC-38 cells labeled with CFSE were allowed to adhere overnight before co-culture with NK cells and FIST15 or control cytokines. MC-38 cells were also susceptible to NK cell-mediated lysing in the presence of FIST15, despite their reported MHC-I expression. However, increased concentrations of FIST15 were required to induce comparable lysis to B16-F0 cells. Despite the increased concentration required, FIST15 remained more potent at inducing MC-38 cytolysis compared to IL15 and sTβRII, achieving an IC50 approximately 12-fold lower (8.73 pM, FIST15 vs 104.32 pM, IL15+sTβRII). Due to the increased cytolytic capabilities of FIST15 treated NK cells observed; the effect of FIST15 treatment on the expression of effector molecules associated with cytotoxicity was investigated. Significantly higher surface expression of death receptor ligands, such as Fas ligand, and the NK cell activating receptor, NKG2D, were found on the surface of FIST15 treated NK cells, compared to controls. Intracellularly, FIST15 treated NK cells produced significantly higher amounts of granzyme B, a serine protease released from cytotoxic granules, which activate caspases in target cells to initiate apoptosis. To determine if this was the mechanism by which FIST15 treated NK cells induced B16-F0 cell death; a fluorochrome-based cytotoxicity assay was utilized to measure the activity of granzyme B and caspase 6 in B16-F0 cells co-cultured with NK cells and FIST15 or controls. Higher serine protease activity was found within B16-F0 cells cultured with NK cells and FIST15 compared to controls.

FIST15 Anti-Tumor Effect in Immunodeficient Mice

Figure 3C:
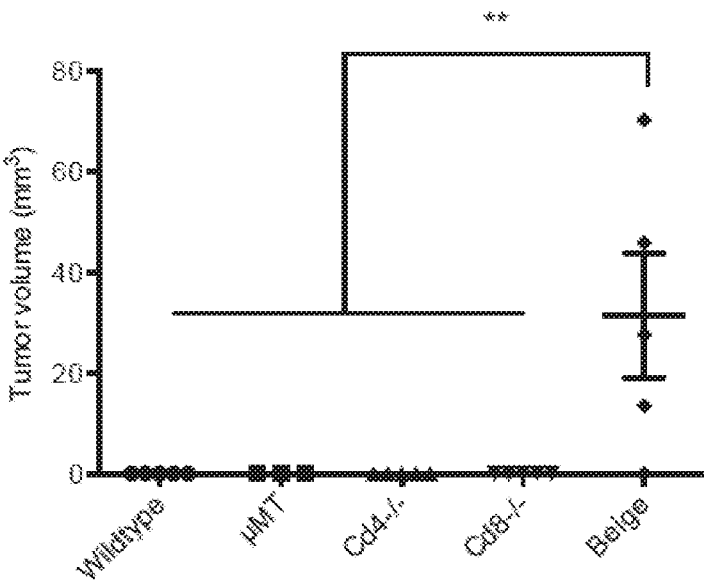
FIG. 3C show tumor volume that was measured on day 7 post-implantation where syngeneic mouse strains lacking CD4+(Cd4−/−), CD8+(Cd8−/−) T cells, B cells (µMT), or functional NK cells (Beige) were implanted with 1×10⁶ B16-FIST15 cells.
Figure 3D:
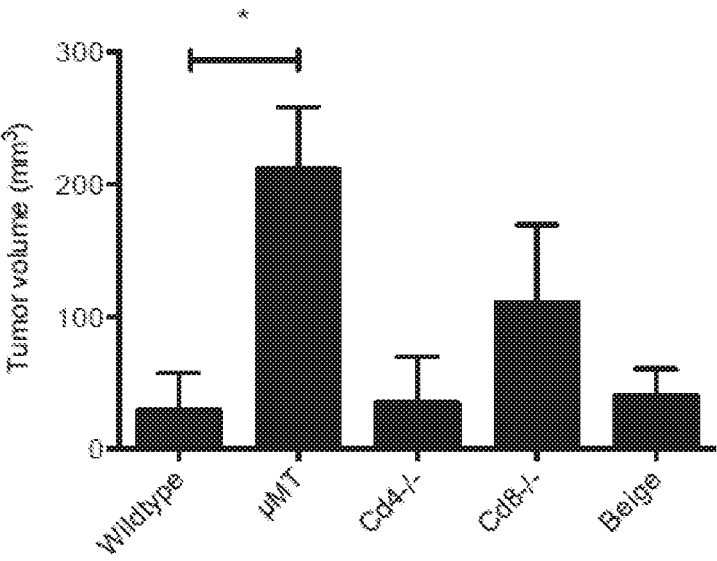
FIG. 3D is a graph showing tumor volume at day 12 post-rechallenge where genetic knockout strains receiving B16-FIST15 were rechallenged 14 days post-implantation with 1×10⁶ B16-F0 cells.

In order to test the anti-tumor effects of FIST15 expression in vivo, the effects of locoregional FIST15 expression were determine in the tumor microenvironment. retroviral-transduced B16-F0 cells were generated with a construct encoding FIST15 cDNA. These cells, B16-FIST15, displayed similar in vitro growth kinetics to mock transduced B16-F0 cells, but failed to form tumor in vivo in immuno-competent mice (FIG. 3A). Mice receiving B16-FIST15 tumor cells were also protected against subsequent rechal-lenge by wildtype B16-F0 melanoma cells (FIG. 3B). Mechanistically, the immune cells that mediated FIST15's anti-tumor effect were determined through the use genetic knockout mouse models lacking individual lymphomyeloid subsets. It was found that only the lack of functional NK cells allowed for the establishment of tumors by B16-FIST15 cells (FIG. 3C). In contrast, lack of CD4+, CD8+ T cells, or B cells did not affect the ability of mice to mount anti-tumor responses against B16-FIST15 cells. these genetic knockout strains that had received B16-FIST15 cells were rechallenged with wildtype B16-F0 tumor and found that a lack of B cells resulted in significantly greater tumor growth (FIG. 3D).

FIST15 Treatment Significantly Inhibits Growth of Estab-lished B16-F0 Tumors

Figure 4A:
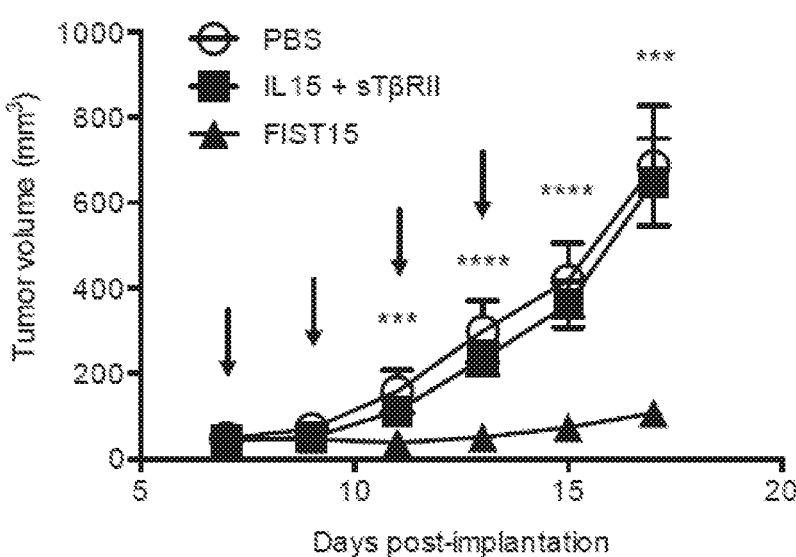
FIG. 4A shows data indicating FIST15 treatment inhibits tumor growth and improves overall survival in mice with established B16-F0 melanoma. Wildtype C57BL/6 mice were implanted with 1×106 B16-F0 cells subcutaneously. Day 7 post-implantation, once palpable tumor had formed, mice were randomized into treatment groups receiving: PBS (n=7), IL15+(n=9), and FIST15 (n=11). Mice were given intraperitoneal injections every second day for 1 week (4 doses total, indicated by arrows) and monitored for tumor growth. Graph of a representative experiment measuring tumor volume±SEM is shown.
Figure 4B:
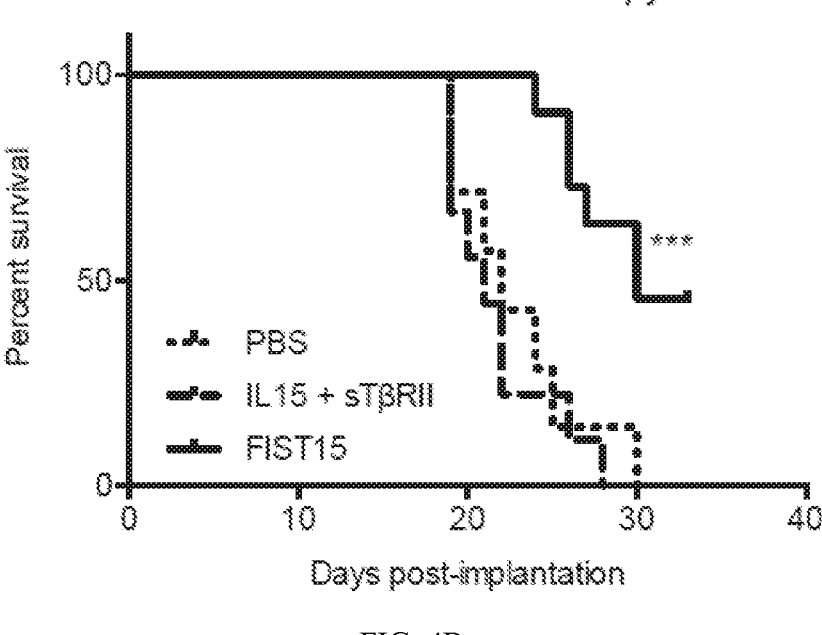
FIG. 4B shows the survival of mice in the three groups depicted in a Kaplan-Meier curve.

To test the efficacy of FIST15 as a therapeutic agent in the setting of established tumor, $1 \times 10^6$ wildtype B16-F0 cells were implanted subcutaneously into the flank of immuno-competent C57BL/6 mice and waited seven days for visible tumor to form. Tumor-bearing mice were then treated with intraperitoneal administration of FIST15, IL15 and sTβRII, or PBS every second day for 7 days (4 doses total) and monitored the mice for tumor progression and survival. FIST15 treated mice displayed a significant delay in tumor growth compared to PBS and IL15 and sTβRII treated mice (FIG. 4A). We also observed a significant improvement in overall survival of FIST15 treated mice compared to con-trols (FIG. 4B).

---

The invention claimed is:

1. A conjugate comprising a polypeptide fragment of type II TGF-beta receptor that specifically binds TGF-beta; a polypeptide fragment of a sushi domain of the IL-15 receptor alpha chain that specifically binds IL-15; and a polypeptide fragment of IL-15, wherein the conjugate has greater than 90% sequence identity to TIPPHVQKSVNND-MIVTDNNGAVKFPQLCKFCDVRF-STCDNQKSCMSNCSITSICEKPQE VCVAVWRKNDEN-ITLETVCHDPKLPYHDFILEDAASPKCIMKE-KKKPGETFFMCSCSSDECND NIIF-SEEYNTSNPDGTGGSSGITCPPPMSVEHADIWVK-SYSLYSRERYICNSGFKRKAGTSSLT ECVLNKATN-VAHWTTPSLKCIRDPALVHQRPAPPSGGSGGG-GSGGGSGGGGSLQNWVNVIS DLKKIEDLIQSMHI-DATLYTESDVHPSCKVTAMKCFLLELQVISLESG-DASIHDTVENLIILANNSL SSNGNVTESGCKE-CEELEEKNIKEFLQSFVHIVQMFINTS (SEQ ID NO: 21).

2. A polynucleotide encoding a conjugate of claim 1.

3. A vector comprising a polynucleotide of claim 2.

4. An expression system comprising a vector of claim 3.

5. A method of treating cancer comprising administering an effective amount of a composition comprising a conjugate of claim 1 to a subject in need thereof.

6. The method of claim 5 further comprising administering the conjugate in combination with checkpoint inhibitors, immunostimulatory cytokines, GM-CSF, anti-PD-1, anti-PD-L1, anti-CTLA-4, anti-CD40, anti-IL-7, or anti-IL-6 antibodies or combinations thereof.

7. A conjugate comprising a polypeptide fragment of type II TGF-beta receptor that specifically binds TGF-beta; a polypeptide fragment of a sushi domain of the IL-15 receptor alpha chain that specifically binds IL-15; and a polypeptide fragment of IL-15, wherein the conjugate has greater than 90% sequence identity to TIPPHVQKSVNND-MIVTDNNGAVKFPQLCKFCDVRFSTCDNQKSCNIS-NCSITSICKPQE VCVAVWRKNDENITLETVCH-DPKLPYHDFILEDAASPKCIMKEKKKPGETFF-MCSCSSDECND NIIFSEEYNTSNPDTIP-PHVQKSVNNDMIVTDNNGAVKFPQLCKFCDVRF-STCDNQKSCMSNC SITSICEKPQEVCVAVWRKNDEN-ITLETVCHDPKLPYHDFILEDAASPKCIMKEKKK-PGETFFMC SCSSDECNDIIF-SEEYNTSNPDGTGGSSGITCPPPMSVEHADIWVK- SYSLYSRERYICNSGFK RKAGTSSLTECVLNKATN-VAHWTTPSLKCIRDPALVHQRPAPPSGGSGGGGSGG-GSGGGGS LQNWVNIVISDLKKIEDLIQSMHIDAT-LYTESDVHPSCKVTAMKCFLLELQVISLESG-DASHDTVE NLIILANNSLSSNGNVTESGCKE- 5 CEELEEKNIKEFLQSFVHIVQMFINTS (SEQ ID NO: 27).

\* \* \* \* \*